(12) United States Patent
Melikov et al.

(10) Patent No.: US 9,310,088 B2
(45) Date of Patent: Apr. 12, 2016

(54) DEVICE AND METHOD FOR REDUCING SPREAD OF MICROORGANISMS AND AIRBORNE HEALTH HAZARDOUS MATTER AND/OR FOR PROTECTION FROM MICROORGANISMS AND AIRBORNE HEALTH HAZARDOUS MATTER

(75) Inventors: Arsen Krikor Melikov, Taastrup (DK); Shengwei Zhu, State College, PA (US); Zhecho Dimitrov Bolashikov, Copenhagen 0 (DK)

(73) Assignee: Technical University of Denmark, Lyngby (DK)

( * ) Notice: Subject to any disclaimer, the term of this patent is extended or adjusted under 35 U.S.C. 154(b) by 1029 days.

(21) Appl. No.: 13/383,225

(22) PCT Filed: Jul. 14, 2010

(86) PCT No.: PCT/DK2010/050189
§ 371 (c)(1),
(2), (4) Date: Apr. 25, 2012

(87) PCT Pub. No.: WO2011/006509
PCT Pub. Date: Jan. 20, 2011

(65) Prior Publication Data
US 2012/0199003 A1    Aug. 9, 2012

Related U.S. Application Data

(60) Provisional application No. 61/226,542, filed on Jul. 17, 2009.

(30) Foreign Application Priority Data

Jul. 17, 2009  (EP) .................................... 09165736
Mar. 10, 2010  (EP) .................................... 10156062

(51) Int. Cl.
*A61G 10/00*  (2006.01)
*F24F 3/16*  (2006.01)
(Continued)

(52) U.S. Cl.
CPC .............. *F24F 3/1607* (2013.01); *A61G 10/02* (2013.01); *A61G 13/108* (2013.01); *A61L 9/20* (2013.01);
(Continued)

(58) Field of Classification Search
CPC ....... A61G 10/02; A61G 13/00; A61G 13/10; A61G 10/005; A61G 10/04; A61G 13/108; A61L 9/16; F24F 3/1607
USPC .......... 96/223; 55/385.1, 385.2; 454/187, 189, 454/341, 56; 128/205.26; 261/104
See application file for complete search history.

(56) References Cited

U.S. PATENT DOCUMENTS 3,511,162 A * 5/1970 Truhan .......................... 454/187
3,601,031 A * 8/1971 Abel ..................... A61G 10/005
454/187

(Continued)

FOREIGN PATENT DOCUMENTS

CA    2567863 A1    5/2008
EP    0787952 A2    8/1997
(Continued)

OTHER PUBLICATIONS

Launder B.E. et al., "The Numerical Computation of Turbulent Flows," Computer Methods in Applied Mechanics and Engineering, vol. 3(2): 269-289, Mar. 1974.

(Continued)

*Primary Examiner* — Duane Smith
*Assistant Examiner* — Minh-Chau Pham
(74) *Attorney, Agent, or Firm* — Dinsmore & Shohl LLP; Weston R. Gould

(57) ABSTRACT

Disclosed is an air distribution control unit or a filtration/ventilation unit which is portable and/or can be mounted on or integrated in furniture e.g. as a cabinet of at the head region of a bed. The filtration/ventilation unit cleanses air from a person/patient by aspirating the person's/patient's exhalation air into the filtration/ventilation unit. To construct an at least partly isolated area around the patient, filtered air can be directed e.g. vertically out of the filtration/ventilation unit to perform an air curtain. Use of the filtration/ventilation unit reduces the risk of dissipation of air-borne diseases and health hazardous matter, and reduces the amount of air to ventilate a room with patients.

16 Claims, 16 Drawing Sheets

(51) Int. Cl.
*A61G 10/02* (2006.01)
*A61G 13/10* (2006.01)
*A61L 9/20* (2006.01)
*A61G 15/10* (2006.01)

(52) U.S. Cl.
CPC ............. *A61G 15/10* (2013.01); *A61G 2203/46* (2013.01); *A61L 2209/111* (2013.01); *A61L 2209/14* (2013.01)

(56) References Cited

U.S. PATENT DOCUMENTS

| | | | |
|---|---|---|---|
| 3,724,172 A * | 4/1973 | Wood | A61L 10/02 128/205.26 |
| 3,757,495 A | 9/1973 | Sievers | |
| 3,935,803 A * | 2/1976 | Bush | F24F 3/1607 454/189 |
| 4,045,192 A * | 8/1977 | Eckstein | A61G 10/02 261/104 |
| 4,939,804 A | 7/1990 | Grant | |
| 5,129,928 A | 7/1992 | Chan et al. | |
| 5,264,015 A | 11/1993 | Matsui | |
| 5,616,172 A | 4/1997 | Tuckerman et al. | |
| 5,997,619 A | 12/1999 | Knuth et al. | |
| 6,062,977 A * | 5/2000 | Hague | A61G 13/108 454/341 |
| 6,916,238 B2 * | 7/2005 | Korman | A61G 10/04 454/187 |
| 8,465,576 B2 * | 6/2013 | Della Valle | A61G 13/108 454/56 |
| 2002/0098127 A1 | 7/2002 | Bollini | |
| 2002/0121196 A1 | 9/2002 | Thakur et al. | |
| 2006/0053554 A1 | 3/2006 | Acton | |
| 2006/0063966 A1 | 3/2006 | Chan et al. | |
| 2009/0064415 A1 | 3/2009 | Payne et al. | |
| 2010/0047115 A1 * | 2/2010 | Krichtafovitch | A61L 9/16 422/4 |

FOREIGN PATENT DOCUMENTS

| | | |
|---|---|---|
| EP | 1575550 B1 | 2/2008 |
| EP | 2301589 A1 | 3/2011 |
| JP | 61-049948 | 3/1986 |
| JP | 19891114874 | 8/1989 |
| JP | 02045014 A | 2/1990 |
| JP | 05223304 A | 8/1993 |
| JP | 2000-342921 A | 12/2000 |
| JP | 2004-316990 A | 11/2004 |
| JP | 2005-226943 A | 8/2005 |
| JP | 05-080812 B2 | 11/2012 |
| WO | 9428814 A1 | 12/1994 |
| WO | 9525250 A1 | 9/1995 |
| WO | WO02/065972 * | 8/2002 |
| WO | 02075221 A1 | 9/2002 |
| WO | 02096338 A2 | 12/2002 |
| WO | WO2006/133451 * | 12/2006 ............. B01D 46/00 |

OTHER PUBLICATIONS

Hyldgaard C.E., "Humans as a Source of Heat and Air Pollution," Department of Building Technology and Structural Engineering, Aalborg University, Aalborg Denmark, pp. 413-433.

Melikov A. et al., "Measurement and Prediction of Indoor Air Quality Using a Breathing Thermal Manikin," Indoor Air, vol. 17(1): 50-59, Feb. 2007.

Melikov A., "Breathing Thermal Manikins for Indoor Environment Assessment: Important Characteristics and Requirements," European Journal of Applied Physiology, vol. 92(6):710-713, 2004.

* cited by examiner

* The inner survaces in the box after the filter (2) and before the straightener (4) should be made of highly reflective material to enhance the effect of the UVGI lights.

1 Fan
2 Coarse and HEPA/ULPA Filters
3 UVGI light
4 Straightener
5 Guiding veins
6 Damper 1 Fan
2 HEPA Filter
3 UVGI light
4 Sliding latch to regulate opening width.

Fig. 4

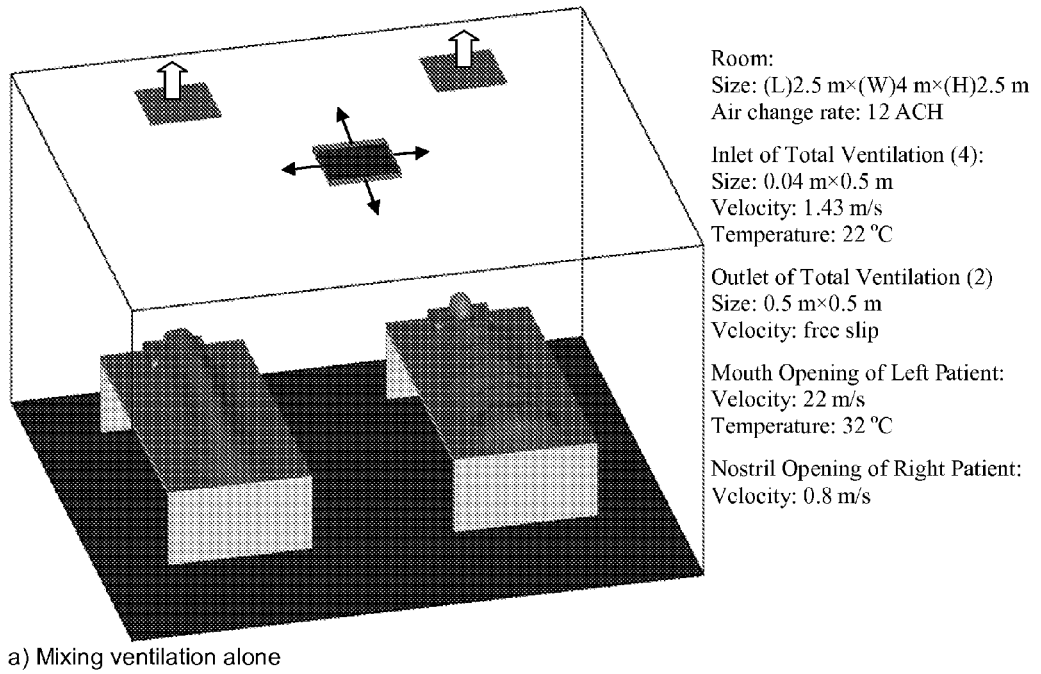

Room:
Size: (L)2.5 m×(W)4 m×(H)2.5 m
Air change rate: 12 ACH

Inlet of Total Ventilation (4):
Size: 0.04 m×0.5 m
Velocity: 1.43 m/s
Temperature: 22 °C Outlet of Total Ventilation (2)
Size: 0.5 m×0.5 m
Velocity: free slip Mouth Opening of Left Patient:
Velocity: 22 m/s
Temperature: 32 °C Nostril Opening of Right Patient:
Velocity: 0.8 m/s a) Mixing ventilation alone

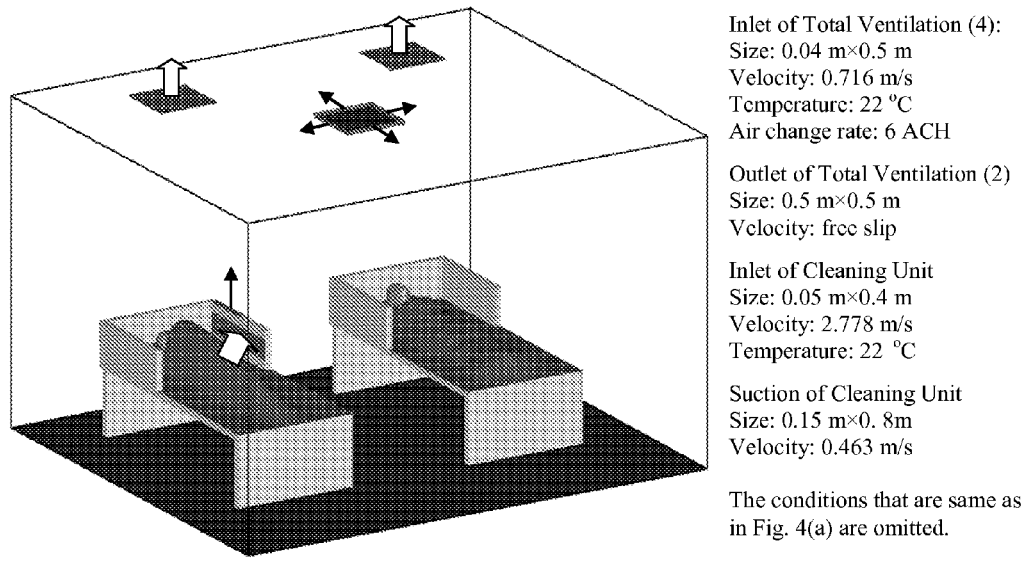

Inlet of Total Ventilation (4):
Size: 0.04 m×0.5 m
Velocity: 0.716 m/s
Temperature: 22 °C
Air change rate: 6 ACH Outlet of Total Ventilation (2)
Size: 0.5 m×0.5 m
Velocity: free slip Inlet of Cleaning Unit
Size: 0.05 m×0.4 m
Velocity: 2.778 m/s
Temperature: 22 °C Suction of Cleaning Unit
Size: 0.15 m×0.8m
Velocity: 0.463 m/s The conditions that are same as
in Fig. 4(a) are omitted.

b) Mixing ventilation with Hospital Bed Integrated Cleaning Unit

Fig. 5
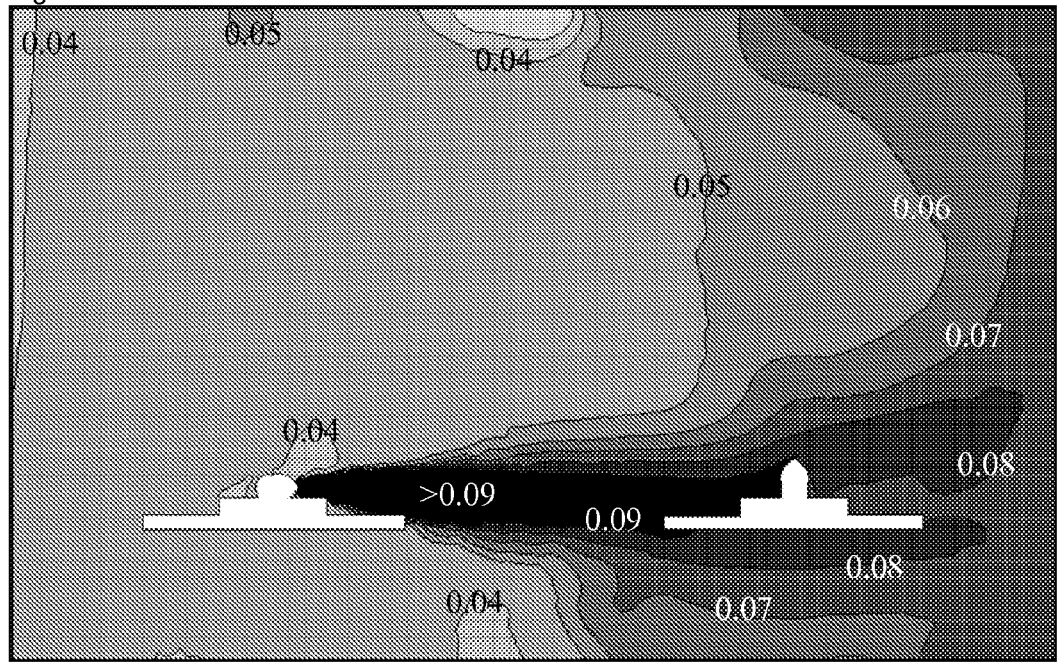
a) Concentration distribution in Sec.0.2x
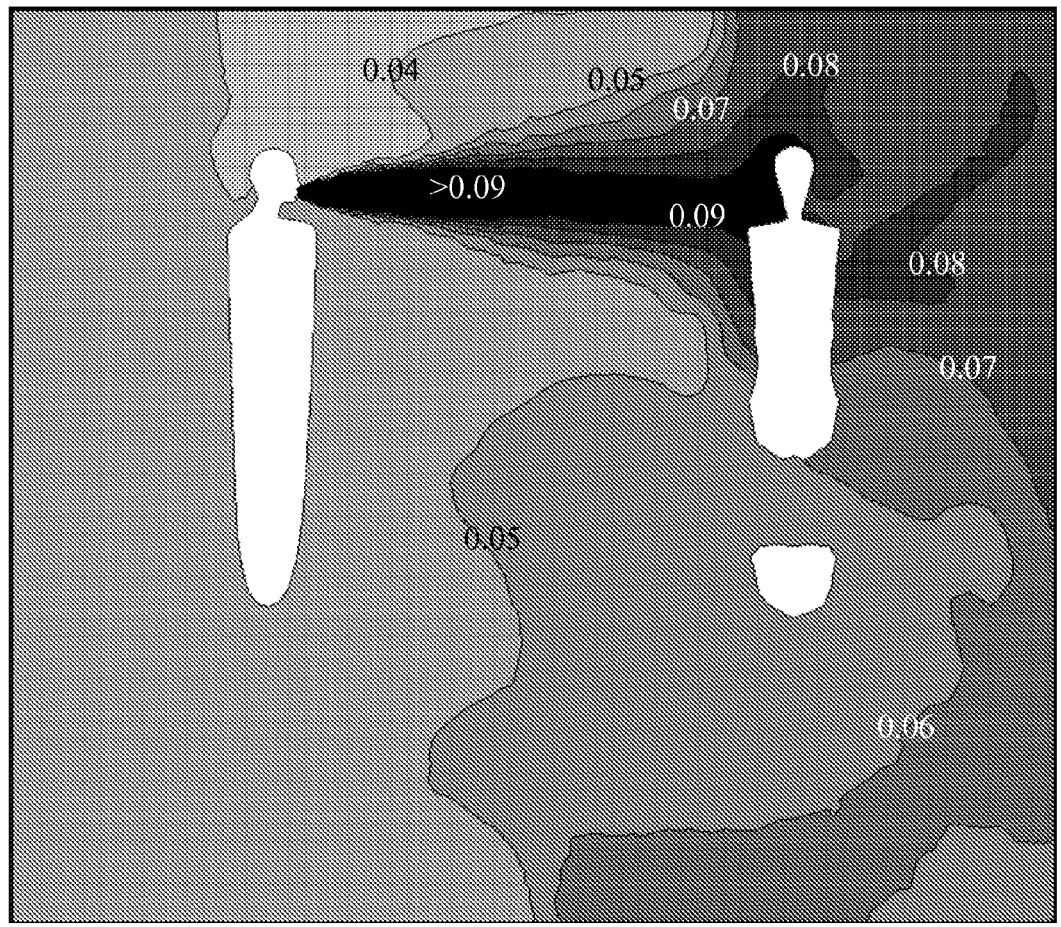
b) Concentration distribution in Sec.0.66z Fig. 6
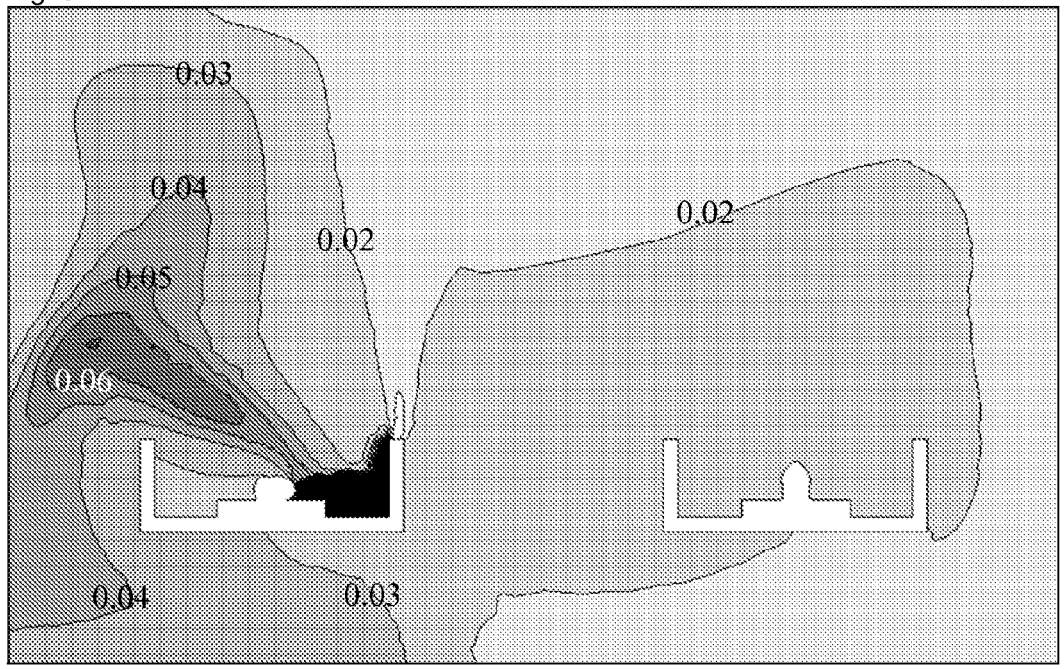
a) Concentration distribution in Sec.0.2x
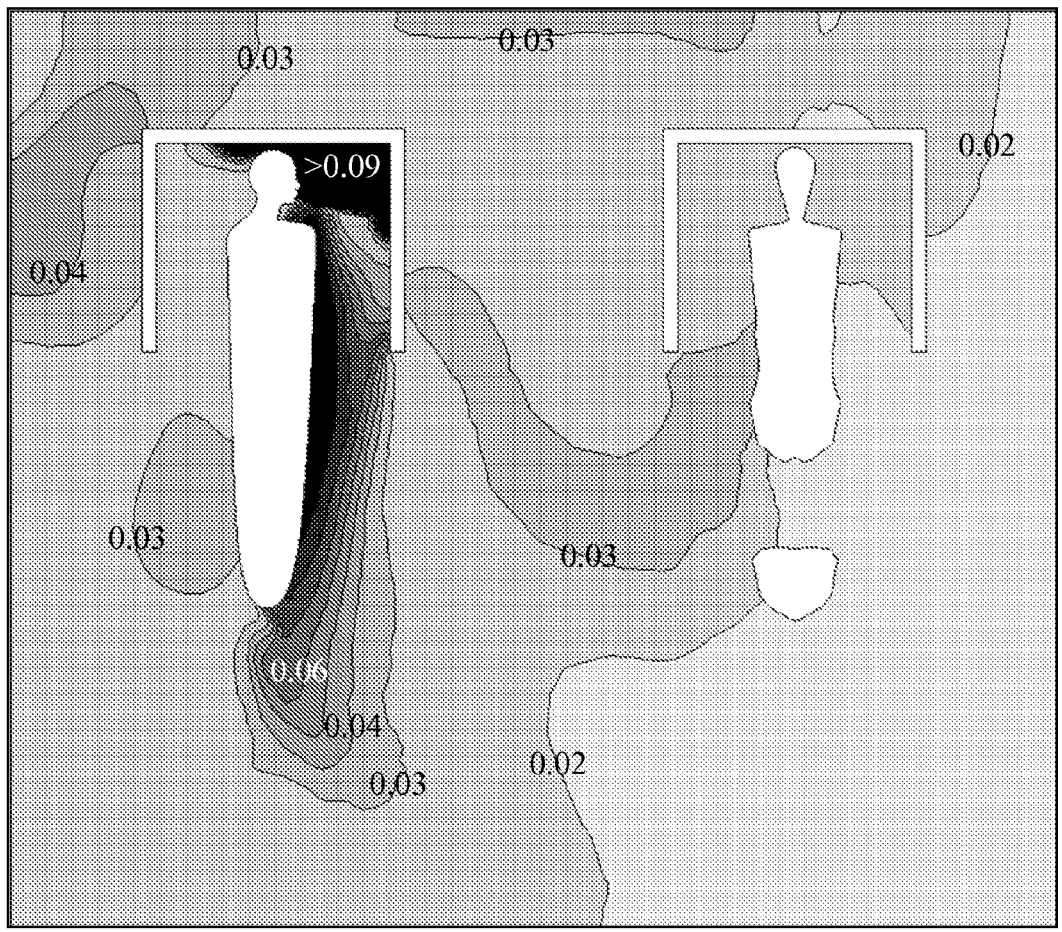
b) Concentration distribution in Sec.0.66z

*Filtration/ventilation unit incorporated in a niche wall
**Hospital bed

1 Patient in bed
2 Filtration/Ventilation unit
3 Docking end to exhaust
* All discharge(supply)/suction(exhaust) openings of 2 have guiding louvres.

1 filtration/ventilation unit
2 dental chair with patient
3 adjustable telescopic air distribution head

Dental Chair Application

DEVICE AND METHOD FOR REDUCING SPREAD OF MICROORGANISMS AND AIRBORNE HEALTH HAZARDOUS MATTER AND/OR FOR PROTECTION FROM MICROORGANISMS AND AIRBORNE HEALTH HAZARDOUS MATTER

CROSS-REFERENCE TO RELATED APPLICATIONS

This application is the U.S. National Phase of PCT/DK2010/050189 filed Jul. 14, 2010, which claims priority of European Patent Application 09165736.1 filed Jul. 17, 2009; U.S. Provisional Patent Application 61/226,542 filed Jul. 17, 1009; and European Patent Application 10156062.1 filed Mar. 10, 2010.

All patent and non-patent references cited in the present application, are also hereby incorporated by reference in their entirety.

FIELD OF INVENTION

The present invention relates to a filtration and ventilation unit, a filtration and ventilation system and a method for ventilating and cleaning the air and minimising the risk of microorganisms, viruses or any other health hazardous airborne matter to dissipate from one person to other persons. The filtration/ventilation unit and filtration/ventilation system is capable of removing and/or filtering output air e.g. exhalation air within short distance from the source (individual) providing the output air. The filtration/ventilation unit and filtration/ventilation system is also capable of producing an air curtain which can partly isolate an area to be cleaned from microorganisms, viruses and/or any other health hazardous airborne matter or an area to be free of microorganisms, viruses and/or any other health hazardous airborne matter. The present invention also relates to evacuating the air exhaled or coughed by an infected patient, purge it from airborne pathogens and health hazardous matter and direct it upwards beside the bed, from one or more horizontal slots, towards the upper levels of the room where it can be mechanically exhausted by total volume ventilation or local exhaust ventilation.

BACKGROUND OF INVENTION

There exists a need for isolation and/or protection of patients, doctors, nurses, visitors, people in close proximity to toxic materials etc. from obtaining airborne diseases or intoxication due to microorganisms, viruses and/or hazardous particulate matter spread via the air. The need for protection of healthy people or the need for cleaning exhaled air is obvious with respect to highly infective viruses such as the flu virus A H1N1 or other swine influenza viruses such as mutated swine influenza viruses, SARS (Severe Acute Respiratory Syndrome) or other coronaviruses, highly pathogenic H5N1 virus or other bird influenza viruses, such as other mutated bird influenza viruses, terrorist attacks with biological weapons (anthrax, small pox), drug resistant tuberculoses, staphylococci etc. Also with respect to the persons suffering from less severe diseases, the protection of those people taking care of the patients or protection of the patients themselves may be of crucial importance to reduce the risk for the patients to catch other diseases.

Ventilation by aspirating air through an exhaust e.g. located in the ceiling is generally used for performing indoor cleaning of air. However, the airflow towards the exhaust opening is not effective for removing contaminated air delivered by e.g. a diseased patient 1-4 m from the exhaust opening.

In respect of the airflow close to the exhaust, the contaminant-capturing efficiency of an exhaust depends on the exhaust design, the positioning near the contaminant source (e.g. sick patient with airborne contagious disease) and the exhaust airflow. The flow of a point exhaust can be used to approximate the air flow in the vicinity of an exhaust opening projecting over a surface. A point sink will draw air (Q) equally from all directions through an area equal to that of an imaginary sphere of radius, r. The radial velocity, $v_r$, of the sink is given as: $v_r = Q/(4\pi r^2)$. The air movement in the vicinity of exhausts is quite complex. Generally, the air velocity distribution across an exhaust surface is not uniform and is influenced by wake formation near the sides of the exhaust or flow contraction, which results in reduction of the effective face area of the exhaust. This leads to fast velocity decay as moving further away from the exhaust surface (FIG. 24).

An alternative to ventilation by exhausting air has been to use isolation rooms for patients being infected by life-threatening airborne diseases. Generally, the aim of infectious isolation unit/room ventilation is to protect or isolate the rest of the hospital from airborne transmission of pathogens exhaled or coughed by the sick patients. Nevertheless, medical staff working in infectious isolation units is under elevated risks of getting sick and spreading the disease. Recent multi-drug resistant strains of tuberculosis have increased the importance of air change rates, filtration, air distribution designs and pressurization.

Today, in infectious wards mixing type of air distribution is used. This can be obtained by exhausting air from a room through ventilation diffusers positioned in or just below the ceiling of the room and at the same time supplying the room with clean air. The clean air supplied at high velocity promotes mixing of the air in the room, and thus dilutes the airborne pathogens and evacuates them out of the room. The problem is that with perfect mixing the concentration of pathogens in the room would be the same in the whole occupied space. Hence to reduce the risk of airborne transmission of infection one needs high air change rates. The more air supplied, the better the dilution. Air-changes of minimum 12 per hour are recommended for isolation hospital wards to dilute the airborne pathogens (ASH RAE Handbook 2007, ISIAQ Review 2003). Some guidelines even recommend as much as 15 air changes per hour as a minimum requirement (WHO 2002). It is evident that the recommended high flow rates will imply quite a lot of energy consumption to condition the air in isolation rooms within the recommended range of indoor temperatures of 21-24° C. Also the ducting, fans and HVAC (heating, ventilation and air-conditioning) unit required for the ventilation systems would be expensive and would occupy quite a lot of space. Another important issue is that this kind of ventilation works with 100% outdoor air, which additionally raises the running costs of the units and make them quite energy inefficient. Use of HEPA filters themselves could become source of secondary spread of pathogens if not changed on regular bases. Usually they are situated out of the ventilated area which elevates the risk of contamination and thus infection. This is another cost related issue for the maintenance of such a system. The use of UVGI when placed in the ventilated area is not quite efficient because the source generating pathogens is located in the lower height of the ventilated space while the UVGI unit for safety reasons is typically installed far way in the upper zone (not lower than 1.7 m above the floor).

Some of the pulmonary activities, i.e. coughing/sneezing, generate quite strong air movement with initial velocities as high as 30 m/s, that completely destroy the ventilation air pattern in the rooms and enhance the airborne cross-infection risk among occupants. To remedy the problem inherent in hospital ventilation systems for infectious isolation units the present invention can be incorporated in the patient's bed or can be secured to the patient's bed. The ventilation units close proximity to the head of the sick person guarantees successful evacuation of the largest part of the pathogen laden air from pulmonary activities, purging it and directing it e.g. upwards, through one or more horizontal slots, towards the exhaust vents of the total volume ventilation at elevated velocities.

Especially in hospitals, crowded and highly visited places and other buildings or equipments subjected to ventilation, the method described herein may allow for considerable energy savings otherwise used for conditioning outside air supply, by reducing as much as two times the need of fresh air for the total volume ventilation. Furthermore, the method ensures much cleaner air in rooms compared to mixing ventilation alone, and thus reduces airborne transmission of infectious diseases to the hospital staff (doctors, nurses, etc.), in clean rooms to immunocompromised patients (HIV positive or with congenital immune disorders), or in other rooms or areas where people may come close to each other.

Herein below a situation as well as a simulation of air distribution from a hospital is described, although the invention herein described can be used in different applications or locations where people come relatively close to each other or come into contact with each other. Examples of such applications or locations where the filtration/ventilation unit or a combination of several units and the system described herein can be used are in hospitals of different kinds, aeroplanes, waiting rooms, trains, busses, restaurants, dental clinics, beds in hotels, beds in homes for elderly people, wheelchairs, nurseries, animal farms (installed for protecting farmers and animals), public toilets etc. However, the filtration/ventilation unit as described herein can also be used to protect subjects and individuals with weak immune system, in the handling of food or food ingredients or in the production and/or wrapping up of food ingredients, food, beverages, pharmaceuticals (pills, vaccines etc), cosmetics, electronic and computer components etc. The filtration/ventilation unit can also be used to remove flavours and/or smells generated in kitchens or kitchen areas, productions that involve handling of obnoxious gases or smells, etc.

Prior art products exists which are ventilators that clean the air, however, these ventilators do not produce an air curtain which can be used to partly or fully isolate an individual which is diseased, or which is at risk of obtaining a disease due to the spread of airborne infections.

When handling food products and infectious air gets into contact with the food ingredients, food or beverages a contamination may occur making the product unsalable due to growth of microorganisms, etc. or the product may become unsafe to eat. The filtration/ventilation unit as described herein may thus be used for a large number of applications within food products or food production such as exhaust of micro-organisms, etc., exhaust of flavours, inflow of air or gas e.g. a gas with a specific composition such as air with an increased amount of oxygen, shielding of one or more individuals, shielding of items such as food products.

SUMMARY OF INVENTION

The present invention relates to an air distribution control unit or a filtration and ventilation unit, a filtration and ventilation system and a method for ventilating and cleaning the air and minimising the risk of microorganisms, viruses or any other health hazardous airborne matter including particulate matter to dissipate from one person to other persons, to dissipate from persons to items, from items to persons or from item to item, to minimising flavour, smell or quality problems and/or to provide items or persons with air or with a gas of a controlled composition.

The invention in the form of an air distribution control and/or filtration/ventilation unit for filtration of air, may comprise A cabinet,
at least one first air slot in the cabinet for directing air into and/or out of the filtration/ventilation unit,
at least one fan for directing air through the cabinet,
at least one means for killing or inhibiting the growth capability of microorganisms or virus present in air, the means for killing or inhibiting the growth capability of microorganisms or virus being located inside of the cabinet and/or being a part of the inner surface or the cabinet,
at least one second air slot in the cabinet for directing air into and/or out of the filtration/ventilation unit, and wherein
the filtration/ventilation unit is portable and/or
the filtration/ventilation unit is capable of directing cleansed output air in a predetermined direction or in predetermined directions.

The air distribution control and/or filtration/ventilation unit may be a moveable unit with any combination of features as described herein. The unit may be with wheels, may be portable, may be with fastening means and/or may be with multiple possibilities for directing air through different numbers of inlet slots and outlet slots. Hereby the unit may be designed to be used in multiple locations or a unit may be designed for only one or a few locations.

The filtration/ventilation unit may also comprise at least one means capable of emitting electromagnetic waves at a wave length having a disinfecting effect on microorganisms or viruses being present in air directed through the cabinet (such as UV lights) or other cleansing techniques, the at least one means capable of emitting electromagnetic waves or other cleansing methods may be located inside of the cabinet.

One or more of the air distribution control and/or filtration/ventilation units can be used to produce an air distribution system or a filtration system. The system may be designed to a multiplicity of locations where air can be used to isolate or partly isolate a volume or the air is used to direct microorganisms, viruses and/or any other health hazardous airborne matter towards an inlet of a filtration/ventilation unit.

The filtration/ventilation unit is described to be capable of directing cleansed output air in a predetermined direction or in predetermined directions. A predetermined direction depends on the situation and the location where the unit is used. When used at a bed the predetermined direction(s) may be vertical upward and/or horizontal. When used in aeroplanes, one unit can be installed in the back of the front seat and a second unit may consists of two sections at the two sides of the passenger's head, for example it can be installed on the seat head rest. In this case the air flow generated by the unit with two sections at the head side will assist the coughed/exhaled air to be successfully moved towards and exhausted by the unit located in the back of the front seat, or vice versa clean air supplied against the passenger from the unit installed in the back of the front seat will transport the coughed/exhaled air backwards to the two sections installed at the two sides of the head where it will be evacuated. The unit installed at the head region can be designed to be used alone. In this case the two sections of this unit (left and right side of the head) can perform independently, i.e. one section supplies ventilation air and the second section sucks the ventilation air mixed with contaminated exhaust air. In both solutions the cleansed air can be discharged below the seat or upward to the baggage compartment of the cabin or re-circulated below the floor of the cabin. When used at a dental chair, the predetermined direction may be horizontal if the patient itself is lying horizontal. Also an inclined or diagonal direction of the cleansed output air may be predetermined direction(s).

A method for controlling air distribution and/or partly isolating an area and/or removing microorganisms and/or viruses in air from an area is also described. The method comprising Localise an area which is to be partly isolated,
providing at least one portable filtration/ventilation unit,
Establishing a filtration system around or in connection to the area,
Directing air from the area into the at least one filtration/ventilation unit,
Directing air out of the at least one filtration/ventilation unit in a direction of between 0° to 360° when compared to the overall or central direction of air being directed into the filtration/ventilation unit and/or directing air out of the at least one filtration/ventilation unit and further into pipes directing the air to a larger ventilation system, hereby
Partly isolating the area and/or removing microorganisms and/or viruses in air from the area.

One possibility for use of the air distribution control and/or filtration/ventilation unit is in or for a bed. At least one filtration/ventilation unit may be located at least at the head region of the bed, where it can be an integrated part of the bed or it can be releasable mounted on the bed. Such a bed can be used e.g. at hospitals to reduce spreading microorganisms, viruses or any other health hazardous airborne matter from one person to other persons.

DESCRIPTION OF DRAWINGS

FIG. 4 illustrates a schematic presentation of a hospital room with: a) Mixing ventilation alone, b) Mixing ventilation with the cleaning (filtration) unit installed in units (boxes) at the head of the patients.
FIG. 5 illustrates computer simulated distribution of coughed air from a patient to another patient and in a room with mixing ventilation alone 12 ACH (air-changes per hour).
FIG. 6 illustrates computer simulated distribution of coughed air from a patient to another patient and in a room with two beds with the cleaning (filtration) unit installed in cabinet around the head of the patients and with mixing ventilation at 6 ACH (air-changes per hour) in the room.

DETAILED DESCRIPTION OF THE INVENTION

Figure 1:
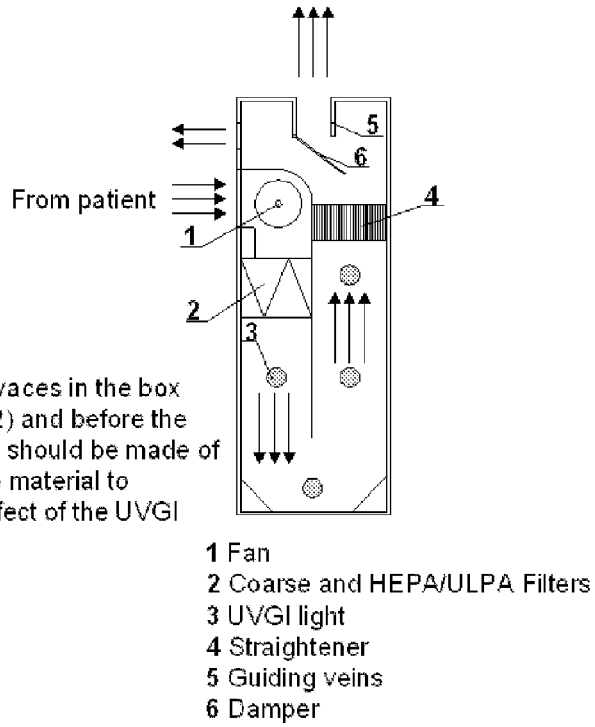
FIG. 1 Set-up of a filtration/ventilation unit.

An aspect of the invention relates to an air distribution control and/or a filtration and/or ventilation unit for filtration and/or ventilation of air, the filtration/ventilation unit comprises a cabinet,
at least one first air slot in the cabinet for directing air into and/or out of the filtration/ventilation unit,
at least one fan for directing air through the cabinet,
at least one means for killing or inhibiting the growth capability of microorganisms or virus present in air, this means for killing or inhibiting the growth capability of microorganisms or virus being located inside of said cabinet and/or being a part of the inner surface or the cabinet,
at least one second air slot in the cabinet for directing air into and/or out of the filtration/ventilation unit, and wherein
the filtration/ventilation unit is portable and/or
the filtration/ventilation unit is capable of directing cleansed output air in vertical and/or horizontal direction or at least at any arbitrary angle between vertical and horizontal direction via guiding vanes and/or
the filtration/ventilation unit when in use produces an air curtain outside of the filtration/ventilation unit with air directed through the second or more air slots.

Preferably the first air slot is used for directing air into the filtration/ventilation unit and the second air slot is used for directing air out of the filtration/ventilation unit. Additional slots may other ways depending on their use.

Herein below, the filtration/ventilation unit is described especially in connection with a bed for a sick patient, however, in respect of many of the features of the filtration/ventilation unit similar features may be relevant for a filtration/ventilation unit used for the protection and/or isolation of one or more items such as food and other items described elsewhere herein.

In a preferred embodiment at least part of the air being directed out of the filtration/ventilation unit is used for creating an air curtain.

By "air curtain" is meant a jet of air blown across an opening or space to prevent or reduce the ingress (penetration) of air or air-borne particles from outside the building envelope or between two zones in a building or occupied space.

The velocities of the air stream producing the air curtain can be up to 5 m/s initial velocity of the air curtain. The initial velocity is determined at the opening (supply) from where the jet stream gets out. Preferred velocities of the air stream are up to 3 m/s initial velocity of the air curtain. However, the velocity of the air stream may be dependent on the purpose of making the air curtain.

For a curtain with initial velocity of $v_o = 3$ m/s at the supply and dimensions of the discharge slot (second air slot) of 0.05 m (width) and 0.50 m (length), $v_{50}\% = 1.5$ m/s is achieved at height of 2.45 m above the discharge slot using the theory for three-dimensional jets (Awbi 2003).

When the ratio of the length to the width of the supply nozzle/discharge slot/second air slot is 10 and with initial velocity of 3 m/s the velocities on the axis of the curtain at different distance from the supply nozzle can be predicted as given in Table 1.

| Height* (m) | Velocity (m/s) |
|---|---|
| 0 | 3.00 |
| 0.3 | 2.85 |
| 0.6 | 2.55 |
| 0.9 | 2.22 |
| 1.2 | 2.00 |
| 1.5 (= at the ceiling if bed is 0.9 m from floor and box is attached projecting 0.2 m above the bed) | 1.89 |

*from discharge opening level of the air curtain which for this calculations was 1.1 m above floor. Also total room height was assumed to be H = 2.6 m (standard room height).

An air curtain is established when air is directed out of the second air slot at a high velocity. The velocity of the air producing the air curtain is preferably at least 0.55 m/s, at least 1.4 m/s, or at least 2.8 m/s when leaving the air slot. The mentioned velocities may also be the actual velocities i.e. the velocity of the air producing the air curtain is preferably about 0.55 m/s, about 1.4 m/s, or about 2.8 m/s when leaving the air slot. The velocity can be adjusted by adjusting the fan or by adjusting the width of the second air slot. Preferably the velocity of the air producing the air curtain is below the threshold where a noise e.g. as a whistling occurs. Preferably the velocity of the air is below 6 m/s at the location where the air leaves the air slot. More preferably the velocity is below 5 m/s. Even more preferably below 4 m/s. Further preferably below 3 m/s. The velocity is preferably above 0.1 m/s. Preferred velocities are between 0.5 and 3.5 m/s. More preferred between 1 and 3 m/s. Further preferred are velocities between 1 and 2.5 m/s. Yet also preferred are velocities between 1 and 2 m/s. Preferred velocities of the air stream are up to 3 m/s initial velocity of the air curtain. Higher velocities might affect occupants close to the air curtain and cause local thermal discomfort.

An air curtain produced by a filtration/ventilation unit as described herein preferably has a height of at least 0.5 m measured from the position where the air leaves the filtration/ventilation unit through the at least one second air slot. More preferably the height is at least 0.75 m, such as at least 1 m, e.g. at least 1.25 m, such as at least 1.5 m, e.g. at least 1.75 m, e.g. at least 2 m. The height of the air curtain can be determined to be the height where the air velocity is half the velocity of the air leaving the filtration/ventilation unit.

When using the filtration/ventilation unit for producing an air curtain between two zones where one of the zones comprises a source of contaminated air, the contaminated air is preferably exhausted locally and close to the source, i.e. the patient (human or animal) or item, before the air is cleansed and mixed with the room air.

Figure 19:
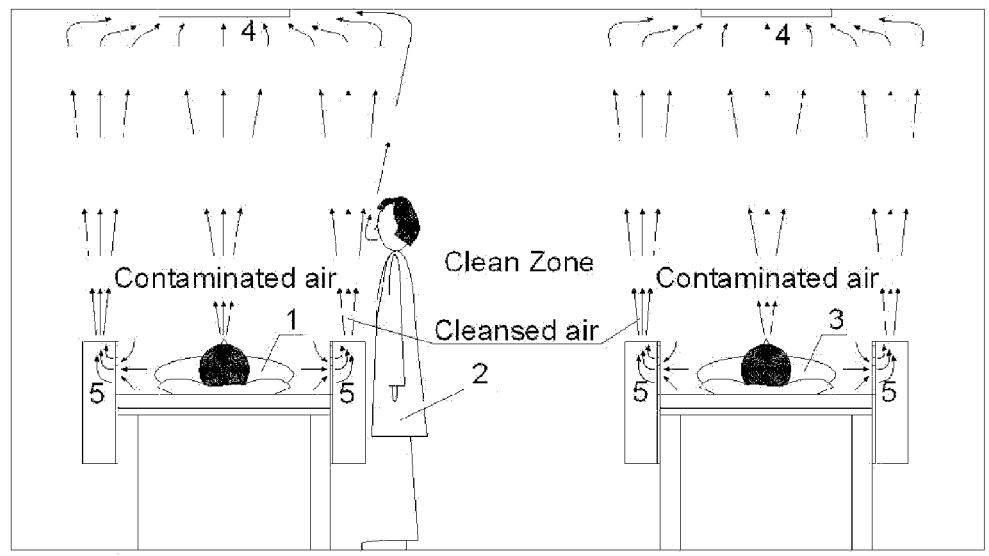
FIG. 19 A room with a filtration/ventilation unit where sick patients are lying in the beds and are coughing or breathing upwards.

The design of the filtration/ventilation unit as described herein ensures optimal airflow distribution: a) in case the sick patient lies on one side the exhaled/coughed air is directed toward the exhaust (first air slot or air inlet) of the unit and this ensures efficient suction without mixing with the room air (FIG. 20); b) when the patient is lying on back and exhales/cough then the generated upward flow is assisted by the upward flow of the cleansed air discharged from the cabinet and is directed towards the exhaust located at the ceiling before it is mixed with the room air (FIG. 19). Similarly in the case with recirculation flow (FIG. 8 *h*) the flow generated by the box is in the direction of the flow of exhalation/coughing and thus assists and helps direct the contaminated airflow toward the suction side of the unit without allowing mixing with the room air. Thus by combining the design of the filtration/ventilation unit as described herein with the short distance from the source of the contaminated air, the cleaning effect of filtration air is increased when compared to cleaning air by ventilation through exhausts of e.g. the ceilings, which might be positioned far away (often above 1 m) from the source of the contaminated air.

To increase protection of an individual (e.g. of a patient being close to one or more filtration/ventilation units, an individual being in a bed next to the patient, a staff inspecting the patient etc), the air curtain is preferably produced from an elongated air slot, however, round—or any other form not having an overall form of elongated—air slots may also be used alone or with more than one air slot being located close to each other. The overall length of an air slot producing an air curtain is preferably at least 15 cm, such as at least 20 cm, e.g. at least 30 cm, such as at least 40 cm, e.g. at least 50 cm, such as at least 60 cm, e.g. at least 70 cm, such as at least 80 cm, e.g. at least 90 cm. With "overall length" is meant the length of a single air slot or the length of smaller air slots located close to each other with an internal distance of less than about 8 cm. Preferably the overall length of an air slot is between 20 and 80 cm, more preferably between 25 and 70 cm, more preferably between 30 and 60 cm.

However, an air curtain may be much longer than the mentioned overall length of an air slot. An air curtain may have a length determined at the air outlet as any of the length mentioned in respect of the air slot. The air curtain can also have a length of at least 1 m, at least 1.5 m, at least 2 m. The purpose of establishing the air curtain may determine the length of the air curtain.

The air slot producing the air curtain is preferably between 1 and 15 mm width, although a width of up to e.g. 40 mm or even higher can be used. The width of the air slot can be regulated by a slide allowing any width between 1 mm and the broadest possible slot of the slot in focus, e.g. such as between 10 and 40 mm. The slide may thus allow a width of between 1 and 15 mm or more. Preferably the air curtain has a width between 1 and 10 mm, more preferably between 1 and 5 mm.

The outer dimension of the cabinet or housing or box may be the outer dimension of the filtration/ventilation unit although e.g. fastening means such as hinges to secure the unit to e.g. furniture and/or handles for carrying the unit may be located at the outside of the cabinet.

The cabinet may have any suitable dimensions although preferred for a box-shaped cabinet is a length of between 10 cm and 250 cm, such as between 11 cm and 225 cm, e.g. between 12 cm and 200 cm, such as between 13 cm and 190 cm, e.g. between 14 cm and 180 cm, such as between 15 cm and 170 cm, e.g. between 16 cm and 160 cm, such as between 17 cm and 150 cm, e.g. between 18 cm and 140 cm, such as between 19 cm and 130 cm, e.g. between 20 cm and 120 cm, such as between 21 cm and 110 cm, e.g. between 22 cm and 100 cm, such as between 23 cm and 90 cm, e.g. between 24 cm and 80 cm, such as between 25 cm and 70 cm, e.g. between 26 cm and 60 cm, such as between 27 cm and 50 cm, e.g. between 30 cm and 40 cm. Preferably the length of a portable cabinet is between 30 and 60 cm.

The cabinet can have a width of between 2 cm and 50 cm such as between 3 cm and 45 cm, e.g. between 4 cm and 40 cm, such as between 5 cm and 35 cm, e.g. between 6 cm and 30 cm, such as between 7 cm and 25 cm, e.g. between 8 cm and 20 cm, such as between 10 cm and 15 cm. Preferably the width of a portable cabinet is between 8 and 20 cm.

The cabinet can have a height of between 5 cm and 80 cm, such as between 7 cm and 70 cm, e.g. between 10 cm and 65 cm, such as between 12 cm and 60 cm, e.g. between 15 cm and 55 cm, such as between 20 cm and 50 cm, e.g. between 25 cm and 45 cm, such as between 30 cm and 40 cm. Preferably the height of a portable cabinet is between 30 and 70 cm.

Any of the dimensions mentioned above in respect of length, width and height of the cabinet may be combined. Dimensions of the cabinet can be 20-150 cm in length, 20-150 cm in height and 2-30 cm width. Preferred combinations of the dimensions of the cabinet shaped as a box are a length of between 30 and 60 cm, a width of between 8 and 20 cm and a height of between 30 and 70 cm. A preferred combination of the dimensions of the cabinet shaped as a box is 0.6 m×0.15 m×0.62 m (length×width×height).

If the entire length of a bed or of an area are to be equipped with a filtration/ventilation unit as described herein, this is possible with one long unit or two or more shorter units. The cabinet may also be cylindrical, cone-shaped or have another shape making it suitable to certain field of application either due to the design or the amount of available space where the filtration/ventilation unit is to be used.

The cabinet has at least one air inlet slot and at least one air outlet slot. More than one of each type of slots may be suitable to obtain better protection/ventilation of an area. Also a slot which functions as an air inlet slot at one time may at another time function as an air outlet slot. Internal air direction devices may determine when a slot functions as an air inlet slot or as an air outlet slot, although also the overall direction of the air being directed through the filtration/ventilation unit may be changed or turned and hereby an air inlet slot can function as an air outlet slot and vice versa. When using the term "slot" or "air slot" this may thus mean "air inlet slot" or "air outlet slot" depending on the direction of the air flow through the filtration/ventilation unit.

The shape of a slot when looking from the outside of the cabinet may be squared e.g. quadratic or rectangular, although other shapes may also be used such as triangular, circular, elliptical or oval-shaped. A slot which at the outside of the cabinet seem to be one slot may be more than one slot e.g. by having the function as an air inlet in part of the slot and the function as an air outlet in the other part of the slot.

Figure 17:
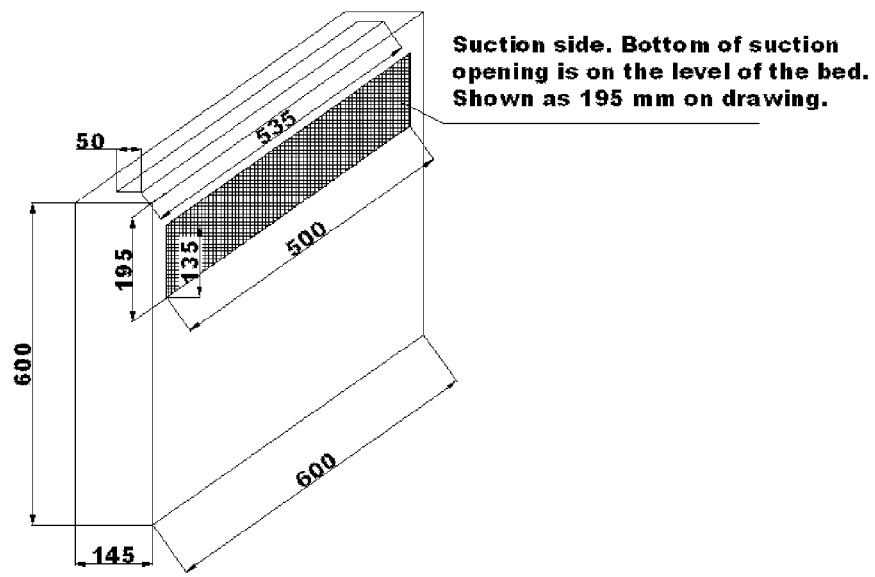
FIG. 17 Perspective view of a filtration/ventilation unit.

The air slots can have any dimensions possible to produce in a cabinet of a certain dimension. Preferably the length of an air slot is 5-20 cm less than the length of the cabinet, the high of an air slot for receiving the diseased air (i.e. a first air slot) is preferably 30-50 cm less than the height of the cabinet, and the width of an air slot for directing the air out of the cabinet (i.e. a second air slot) is preferably 5-15 cm less than the width of the cabinet. As an example a filtration/ventilation unit with a cabinet of 0.6 m×0.15 m×0.62 m (length×width×depth/height) can have a first slot (air inlet) of 0.50 m×0.14 m (length×width) and a second slot (air outlet) of 0.54 m×0.05 m (length×width). The air slots may be positioned as indicated in FIG. 17.

Figure 18:
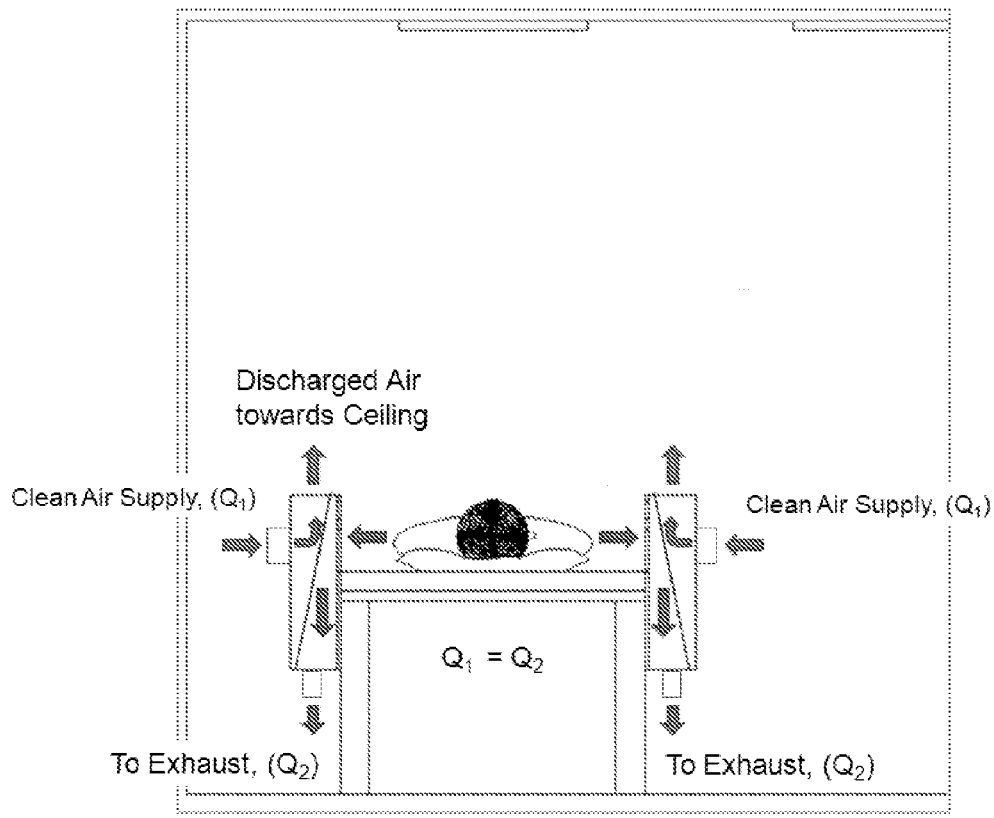
FIG. 18 A room with a filtration/ventilation unit on each side of a patent.

A filtration/ventilation unit with a cabinet of 0.6 m×0.15 m×0.62 m (length×width×depth/height) can also have two first slots (air inlet) each of 0.50 m×0.14 m (length×width) and a second slot (air outlet) of 0.54 m×0.05 m (length×width) as well as an air outlet to an exhaust. Possible location of the air slots can be seen in FIG. 18, however, the use may also be for other situations mentioned herein and not only for a bed as indicated in FIG. 18. The exact distances of the air slots to the edges may be as indicated in FIG. 17.

A filtration/ventilation unit with two air inlet slots and two air outlet slots or one air outlet slot and one connection to an air exhaust as shown in FIG. 18 can be sectioned into two sections by a partition positioned diagonally between two corners of the interior of the filtration/ventilation unit. Such a partition is made of an air-tight material, avoiding mixing the air in the two sections.

In an embodiment the at least one first air slot and/or the at least one second air slot have guiding means for guiding the direction of the air when the air goes out of the air slot. The guiding means e.g. vanes may be positioned parallel or perpendicular to the length side of the slot or a slot may both have guiding means positioned parallel and perpendicular to the length side of the slot, where the parallel and perpendicular guiding means are located beside each other to make it possible to direct a part of the outlet air in one direction and another part of the outlet air in another direction.

Also air inlet(s) may have adjustable guiding means to have the possibility of performing the aspiration from specific locations. The guiding means of an air inlet may be adjusted with the same angles as described elsewhere herein in relation to guiding means guiding outflow air.

The guiding means of a slot may change its position and guide the outflow air in a direction of up to 90° in either direction when compared to a line being perpendicular to the outlet of the cabinet. The outflow direction of the air may be determined manually by adjusting the guiding means e.g. adjustment by turning a knob or the adjustment may be determined automatically by control located in the filtration/ventilation unit. Hereby a filtration/ventilation unit located at a bed can continue to direct the air out of the unit in e.g. a vertical direction even if the head part of the bed is lifted or lowered to raise or lay down the upper part of a patient, respectively.

In an embodiment the filtration/ventilation unit may have a third and/or fourth slot for directing air into and/or out of the filtration/ventilation unit. As described elsewhere herein the number of slots may vary among different filtration/ventilation unit and the air direction may be different and can be adjusted. One or more slots may also be temporally closed e.g. by a damper or by a cap or cover to avoid any inlet or outlet of air through this/these slots. Examples of filtration/ventilation units with two outlets can be seen in FIGS. 8e and 8g.

A second or further air inlet may be used to obtain low air flow into a first or the second air inlet, such that a low air flow is obtained above the head of a patient. By collecting airstreams from the two or more airstreams to a main stream, a high air flow being directed vertically from the filtration/ventilation unit may be obtained.

In a preferred embodiment air is not directed in and out of an air slot at the same time. An exception to this may be if an air slot from the outside of the filtration/ventilation unit seem to be one air slot, but in fact is more than one air slot.

Preferably air inlet slots are not located at the bottom (i.e. the side of the cabinet facing towards the floor when the unit is in function) of a filtration/ventilation unit when the unit only has one air inlet slot. However, if the filtration/ventilation unit is to be located at or above the level of the head of an individual the air inlet slot may be located at another side that the bottom of the filtration/ventilation unit, where the bottom is the side facing the floor when the unit is in function. Preferably the air inlet slot if only one inlet slot is present in the filtration/ventilation unit is not located at the bottom of the cabinet if the unit is to function at a distance below 80 cm from the floor, such as below 60 cm from the floor, more preferably below 40 cm from the floor, further preferably below 20 cm from the floor. If an air inlet is positioned too close to the floor there is a risk of introducing dust and other particles into the filtration/ventilation unit, which can reduce the lifetime of the filters in the unit.

The fan may be capable of directing air either ways through the filtration/ventilation unit. The fan may thus have the capacity to function in both directions. Alternatively, two or more fans can be incorporated in one cabinet. When one cabinet has two or more fans, these fans may be used simultaneously and function together to direct the air in an overall similar direction i.e. a main stream through the cabinet, or one fan is capable to direct air in one direction and the other fan is capable to direct air in the other direction through the filtration/ventilation unit.

The fan or fans of a filtration/ventilation unit may be adjustable in speed. The mean velocity of the air being directed through the cabinet might vary from 0.1 m/s to 10 m/s, e.g. from 0.2 m/s to 10 m/s, such as from 0.3 m/s to 9 m/s, e.g. from 0.4 m/s to 8 m/s, such as from 0.5 m/s to 7 m/s, e.g. from 0.6 m/s to 6 m/s, such as from 0.7 m/s to 5 m/s, e.g. from 0.8 m/s to 4 m/s, such as from 0.9 m/s to 3 m/s. Preferred is a mean velocity of between 0.5 and 3 m/s.

In a preferred embodiment the mean velocity at the inlet is lower that at the outlet. This may be obtained by a larger area of the inlet slot(s) when compared to the area of the outlet slot(s). The velocity of the ingoing air at the inlet slot may be less than 95% of the velocity of the velocity of the outgoing air at the outlet slot, however, the velocity of the ingoing air may also be less than 90% of the outgoing air, such as less than 80%, e.g. less than 70%, such as less than 80%, e.g. less than 60%, such as less than 50%, e.g. less than 40%, such as less than 30%, e.g. less than 20%. Preferably the velocity of the ingoing air is 40-90% of the velocity of the outgoing air. More preferably the velocity of the ingoing air is 45-85% of the velocity of the outgoing air. Even more preferably the velocity of the ingoing air is 50-80% of the velocity of the outgoing air. Yet further preferably the velocity of the ingoing air is 55-75% of the velocity of the outgoing air.

The filtration/ventilation unit can further comprise means for regulating the direction and/or velocity of the air producing the air curtain. These means for regulating the direction and/or velocity of the air producing the air curtain may be automatically regulated to regulate the direction and/or velocity of the air producing the air curtain and this regulation is based on the information determined by the sensors as described elsewhere herein.

The fan of the filtration/ventilation unit may be constructed to be rechangeable and/or easy to clean to avoid/minimise spread of infections, furthermore the means for killing or inhibiting the growth capability of microorganisms or virus e.g. UVGI light would minimise the risk of microbial infestation.

If a filtration/ventilation unit has more than one air inlet and more than one fan, the fans can provide air streams through the two or more inlets and direct these two air streams to a main air stream within the filtration/ventilation unit where filtration and cleansing of the air is perform as described elsewhere herein. An airstream from a single inlet may also be divided into two or more outlets.

If a filtration/ventilation unit has more than one air outlet and more than one fan, the fans can provide air streams out through the two or more outlets.

Air inlet(s) and air outlet(s) of a filtration/ventilation unit may have any suitable dimensions to secure a proper filtration/cleansing process of the air surrounding a subject to be isolated and/or protected from infectious agents of airborne diseases. In an embodiment at least one air inlet could be larger than at least one air outlet. A smaller dimension of an air outlet compared to the dimension of an air inlet may increase the velocity of the air being directed out through the air outlet.

Means for killing or inhibiting the growth capability of microorganisms or virus may be equipped with a cathode material and an anode material forming a galvanic element in contact with an electrolyte. This is further described in EP 1575550. The material as described in EP 1575550 may cover part of or the entire inner surface of the cabinet. The material of EP 1575550 may also be located such that the air stream inside the filtration/ventilation unit is directed through the material e.g. due to a bottleneck/narrowing construction inside the cabinet. The material as described in EP 1575550 may also be incorporated into a filter. The air in the cabinet may pass through this filter.

Means for killing or inhibiting the growth capability of microorganisms or virus may also be a filter. A preferred filter of a filtration/ventilation unit may be a HEPA (H10-H14) or a ULPA (U15-U17) filter. The filter may also be an electrical filter.

A high-efficiency particulate air (HEPA) and ultra low particulate air (ULPA) filters are types of air filter. Air filters remove microscopic particles, such as bacteria, dust mites, and animal dander from the air. HEPA filters can be used in the filtration/ventilation unit as described herein to help prevent the spread of infections, diseases, and/or allergies by removing particles e.g. of 0.3 µm and larger. The range of particles removed by the ULPA filter may be 0.12 µm and larger. To increase the life performance of the HEPA/ULPA filter, a coarser filter plate that can be removable and easy to clean, can be used just at the intake of the filtration/ventilation unit to stop parts of sputum/mucus or saliva generated from coughing sneezing.

A HEPA filter can remove more than 99% of indoor airborne particles that are 0.3 micrometers wide. This includes allergens such as dust mites, pollen, animal dander, and mould, as well as bacteria and viruses. Particles of this size, also called the most penetrating particle size (MPPS), are the most difficult to filter.

The at least one filter of the filtration/ventilation unit may be located in the cabinet at any suitable location e.g. between the inlet slot and the means capable of emitting electromagnetic waves e.g. a UV lamp as described elsewhere herein, a filter may also be located at outlet slot(s). One or more fans may be located between the slot and the filter or between the filter and the means capable of emitting electromagnetic waves.

The filter may have any shape e.g. a shape like the inlet or outlet slot or a shape suitable to secure a simple replacement of the filter. Preferred shapes of the filter are circular, oval or squared.

The filter may be located in a frame making it easy to handle. The frame may comprise one or two curtains (one on each side of the filter) which can be moved manually, or due to removal of the filter from the cabinet be pulled in front of one side or both sides of the filter. The risk of spreading diseases can thus be reduced.

The filtration/ventilation unit may comprise at least one means capable of emitting electromagnetic waves having a disinfecting effect on microorganisms or viruses being present in the air directed through said cabinet. The at least one means capable of emitting electromagnetic waves may be located inside of the cabinet. The means capable of emitting electromagnetic waves may be one or more incandescent lamps, bulbs, LEDs, xenon lamps, halogen lamps, light bulbs such as a UV light bulb. UV light used in the filtration/ventilation unit may have a wavelength between 10 and 400 nm. Preferred is Ultraviolet radiation in the range 225-302 nm as being lethal to microorganisms and which is referred to as ultraviolet germicidal irradiation (UVGI) Preferred is a wavelength of at about 265 nm as this is most destructive to bacteria and virus DNA. To protect the occupants from unwanted irradiation from the UVGI light a UV filter shield may be applied at the exhaust louvers of the device.

Preferred light bulbs are UV-C light bulb emitting 100-280 nm. Also UV-B lights of 280-320 nm can be used.

Within the filtration/ventilation unit the passing air may be subjected to very low exposure times to the UV light. The exposure time may be between 0.1 and 60 seconds, e.g. between 0.15 and 30 seconds, such as between 0.2 and 20 seconds, e.g. between 0.25 and 15 seconds, such as between 0.3 and 10 seconds, e.g. between 0.35 and 5 seconds, such as between 0.4 and 3 seconds, e.g. between 0.5 and 1.5 seconds. Preferred is an exposure time between 0.25 and 1 second. Such short exposure times can be obtained by highly reflective lining of the box inside the UV light compartment.

Treatment time such as form 15 to 30 seconds may result in at least 40% bacteria mortality and bacteria exposed to 254 nm for one minute may result in at least 95% mortality.

The weight of the filtration/ventilation unit as described herein with any of the features described herein may be below 100 kg, e.g. between 1 and 100 kg, such as below 75 kg, e.g. below 50 kg, such as below 40 kg, e.g. below 30 kg, such as below 25 kg, e.g. below 20 kg, such as below 15 kg, e.g. below 10 kg, such as below 9 kg, e.g. below 8 kg, such as below 7 kg, e.g. below 6 kg, such as below 5 kg, e.g. below 4 kg.

A filtration/ventilation unit with wheels may have any weight as described above. If the filtration/ventilation unit is portable the weight is preferably below 15 kg, e.g. below 10 kg, such as below 9 kg, e.g. below 8 kg, such as below 7 kg, e.g. below 6 kg, such as below 5 kg, e.g. below 4 kg. Preferably a portable unit has a weight of 1-10 kg, more preferably of 1-8 kg. A lighter version of less than 1 kg could be achieved with no UVGI inside, this may be relevant if the cabinet is connectable to the total volume ventilation, i.e. supplies air from ventilation and exhausts to ventilation.

As mentioned above the cabinet may comprise at least one fastening means e.g. a hinge to make it possible to attach the filtration/ventilation unit to furniture, ceilings, frames or other types of supports. Also the cabinet may comprise handles for carrying the filtration/ventilation unit.

The at least one fastening means e.g. a hinge may be located at the back of the cabinet and/or at the bottom of the cabinet. The "back of the cabinet" means at the opposite side of the cabinet than where an air inlet slot (which also can function as an air outlet slot) is located. In another embodiment the cabinet can be attached to a device (guiding lines) which allows to glide the unit horizontally and vertically.

The hinges which may be mounted on the cabinet may make it possible to turn the filtration/ventilation unit without removing it from the support whereto it is mounted. E.g. a filtration/ventilation unit with fastening means located at the bottom of the cabinet, and which is mounted on a hospital bed, may be turned nearly 180 degree downward making more space for a doctor/nurse/relative to talk to the patient or to handle the patient. The presence of a track mounted on the furniture or on the cabinet may make it possible to glide the cabinet away from a location and back again at a later time. In respect of a cabinet used on a bed, the bottom of the cabinet is preferably without any outlet slots. Preferably the bottom of the cabinet is also without any inlet slots.

The filtration/ventilation unit may comprise measuring means. The measuring means may be a sensor comprising a camera or an infrared sensor, e.g. infrared temperature sensor allowing for identification of the position of the face of a lying person (i.e. left, right or upwards). Based on an identification of a relevant feature e.g. the position of the face of an individual, a signal may be sent to a computer, which can be an integrated part of the filtration/ventilation unit, the computer may determine when to regulate slots of a relevant filtration/ventilation unit. The regulation may be turning e.g. the direction of the outgoing airflow from a slot or regulate which slots of a unit are to aspirate or blow air. This would imply great energy efficiency and better performance of the suggested system.

The measuring means may detect air stream, temperature, colour, skin versus no skin or skin versus hair e.g. Optical sensors based on reflectivity from hair or skin. The measuring means may also be one or more movement censors. The measuring means may detect velocity due to breathing activities. A $CO_2$ measuring sensor could be used, which would start the exhaust as soon as it senses elevated levels of $CO_2$. Exhaled air contains 40,000 ppm of $CO_2$ so a level above 4,000 ppm may be a threshold for activating the exhaust. Skin temperature sensors or pressure/posture measuring sensors that could be placed in the patients gown/pillow and react on pressing or other means may detect whether the patient is present, and only turn on the filtration/ventilation unit when the patient is present.

A gas supply may be connected to the filtration/ventilation unit to make it possible to control the composition of the air stream leaving the filtration/ventilation unit through the air outlet slot. By supplying outgoing air with oxygen and/or other gasses it is possible to increase the content of oxygen and or other gasses in this air stream. The content of oxygen and/or the other gasses in outgoing air can thus be at least 20%, such as at least 25%, e.g. at least 30%, such as at least 35%, e.g. at least 40%. The filtration/ventilation unit may also be capable of regulating the composition of other gasses in the air curtain, such as the amount of carbon dioxide, and/or nitrogen, NOx and others in the air curtain stream.

The filtration/ventilation unit may also comprise a humidifier for humidifying the air being directed out of the unit.

The filtration/ventilation unit may also comprise heating means for heating the air being directed out of the unit.

Target temperature (average temperature at the cross section of the heated jet at the distance where it first meets the person) when the air of the air curtain is heated should be from isothermal (temperature of the supplied jet equal to room temperature) up to 35° C.

Target temperature (average temperature at the cross section of the cooling jet at the distance where it first meets the person) when performing a cooling of the air before producing an air curtain, should be from isothermal (temperature of the supplied jet equal to room temperature) down to 18° C. Preferably the temperature should not be below 18° C. to avoid local thermal discomfort especially when supplying air to the back at the neck region.

Localized cooling and heating can help to utilize some energy savings by keeping highest indoor temperatures in the summer and lowest in the winter as recommended by ASHRAE 55-2004 and EN 15251-2007.

When using the filtration/ventilation unit as described herein, the total volume ventilation rates as described elsewhere for exhaust and supply can be from less than 1 ACH (Air Change per Hour) up to the values recommended by the standards (ASHRAE 170-2008, DS 2451-9, 2003).

For individuals in need of humid air and/or hot air and/or cold air enveloping the body e.g. patients with severe burnings on their bodies, this may be possible by equipping the filtration/ventilation unit with a humidifier and/or heating means. It is also possible to cool and heat at the same time by incorporating fan coil units or other means.

The filtration/ventilation may comprise means for drying the air passing out of the cabinet and/or means for humidifying air passing out of the cabinet.

The filtration/ventilation unit may also comprise means for regulating the composition of gasses in the air curtain. Hereby the amount of oxygen, carbon dioxide, and other gasses can be regulated by plug connection to an existing gas pipe line (hospitals, factories etc) or to a gas bottle.

The inside of the cabinet may be of a highly reflective material to enhance the effect of the means capable of emitting electromagnetic waves. Especially the surface in the box after the filter and before the straightener can be made of a highly reflective material.

The filtration/ventilation unit may comprise battery/batteries, fuel cells or photovoltaic collectors, e.g. an integrated although exchangeable rechargeable battery. The battery makes it possible to use the filtration/ventilation unit in locations too far away from electricity outputs, or when repositioning a surrounded area/room e.g. repositioning a bed with a patient e.g. from one room to another room.

A filtration/ventilation unit may comprise any features described herein as well as any combination of the described features.

Filtration System

In another aspect the invention relates to a filtration/ventilation system comprising at least one portable filtration/ventilation units as described herein. A filtration/ventilation system can be produced to established a space (area/volume/room) wherein the system is used to reduce spread of microorganisms and airborne health hazardous matter from this space and/or to protect this space from microorganisms and airborne health hazardous matter from the surroundings.

One filtration/ventilation unit located on one side of a bed may be used together with another filtration/ventilation or a ceiling on the other side of the bed to make an area or a room between the unit and the ceiling which is at least partly isolated from the surroundings. The isolation can be formed by a vertical air stream or air curtain from the air outlet of the filtration/ventilation unit.

The filtration system can be at least two portable filtration/ventilation units which are positioned on each side of an area to partly isolate the area from the surroundings and/or on each side of an area being at risk of containing infectious microorganisms and/or viruses to prevent penetration within the room. By the use of at least one or two or more filtration/ventilation units it is possible to partly or fully surround an area to at least partly isolate from the surroundings or protect the surroundings from the area. The isolation from the contaminated room air/isolated area air is performed by producing air streams or air curtains from the air outlet of the filtration/ventilation units.

If the at least two filtration/ventilation units in a filtration system each create a negative pressure in the surrounded area/room, air in this room may be cleansed and thus reducing the risk of spreading infectious organisms including viruses. "Surrounded" is to be understood as creating a room from where only minimal air will escape from the passage through a filtration/ventilation unit. Hereby an area or a room between a wall and a single filtration/ventilation unit or an area or a room between two filtration/ventilation unit is to be understood as a surrounded area/room, although the two filtration/ventilation units may perhaps only constitute in total about e.g. 30-50% of a circle or square/rectangle illustrating a cut through the surrounded area. Thus "surrounded" is not to be interpreted as completely surrounded.

Especially if the at least two portable filtration/ventilation units of a filtration system each direct outlet air substantially vertically out of the filtration/ventilation unit, the surrounded area/room may be partly isolated. The outlet air may be directed in a direction of 20° into or away from the partly isolated area in respect of a vertical air stream to secure a partly isolated area. Although it may also be possible to adjust the direction from 0 to 90° each way in respect of a vertical air curtain, hereby a slot may be adjustable within 180°, such that the out coming jet may be adjusted to hit the rim of the box or adjusted to collide with the body of the person.

In a filtration system comprising at least two filtration/ventilation units at least one of the units may create a negative pressure in the surrounded area and at least one another of the filtration/ventilation units may create a positive pressure in the area (see e.g. FIG. 8a). The positive pressure may constitute an air stream directed from one filtration/ventilation unit towards another filtration/ventilation unit which at the same time produces a negative pressure in the area and thus aspirate air from the surrounded area into the filtration/ventilation unit.

When creating a filtration system wherein at least one filtration/ventilation unit produces a negative pressure and at least one filtration/ventilation unit produces a positive pressure within a surrounded area comprising a source of air (e.g. a breathing individual) located inside of the area, the filtration/ventilation unit producing the negative pressure preferably

- is located closer to the source of air (e.g. the face of an individual) located inside of the area than the at least one filtration/ventilation unit producing a positive pressure and/or
- is located such that at least one air inlet of the filtration/ventilation unit is facing the direction of the air emerging from the source of air located inside of the area.

The described filtration system may be a bed with at least two filtration/ventilation units located at the side head region of the bed, one on each side of a patient. The described filtration system may also be a bed with at least three filtration/ventilation units located at the side head region of the bed, one at the back and one on each side of a patient. A breathing patient is the source of air located inside of the surrounded area. The one filtration/ventilation unit may direct air out of the filtration/ventilation unit where the air passes the head of the patient, the other filtration/ventilation unit aspirate air from the head region of the patient to cleanse the air. Some possibilities with two filtration/ventilation units located at a bed at each side of an individual and with different directions of air streams can be seen in FIG. 8. These situations may be combined with a filtration/ventilation unit located at the end of the bed, behind the head of the individual. Preferably the unit located behind the head of the individual aspirate air parallel to mattress of the bed and produces a vertical air curtain with the air stream going out from the unit.

To make the filtration system flexible in respect of the slots of the filtration units used for ingoing and outgoing air due to the situation e.g. the position of an individual, each filtration/ventilation unit may be connected (wireless or with wire) to a controlling unit. The controlling unit may send signals to each filtration unit to regulate the air streams in respect of direction (out versus in, on versus off, or adjust the angle of the air stream) as well as the velocity of the air streams.

In a filtration system where at least one filtration/ventilation unit produces a positive pressure within a surrounded area and at least one filtration/ventilation unit produces a negative area within a surrounded area, measuring means can be positioned in or close to the filtration system to measure the direction of air emerging from a source of air located inside the surrounded area and wherein the direction of air emerging from a source of contaminated air located inside is used to determine which filtration/ventilation unit or units produce(s) a negative pressure and which filtration/ventilation unit or units produce(s) a positive pressure.

If the source of contaminated air located inside of a surrounded area is a human being, the measuring means may detect which way the head of the patient is directed and hereby determine which filtration/ventilation unit should produce a negative pressure and which should produce a positive pressure. Examples can be seen in FIG. 8.

A gas supply may be connected to the filtration/ventilation unit as described above. Especially in respect of air or a specific combination of gasses passing by the head of a patient e.g. as illustrated in FIGS. 8a, 8f and 8h the air streams directed towards the patient may contain an increased amount of oxygen e.g. in an amount as described above. The air with an increased amount of oxygen may be directed out of the outlet slots in the top part of the illustrated filtration/ventilation units in FIGS. 8a, 8f and 8h and/or out of the outlet slot in the lower part of the outlet slots illustrated filtration/ventilation units in FIGS. 8a and 8h. Oxygen may also be supplied in the example illustrated in FIG. 16. Supply of oxygen may be suitable in other situations such as in rooms where people stay for a longer period such as in aeroplanes, busses, trains, waiting rooms, dining rooms, living rooms, indoor playgrounds etc.

The filtration system may comprise filtration/ventilation units with any features described elsewhere herein and any combination of the described features.

The use of the filtration/ventilation units as described herein may have the influence that smaller dimensions of pipes for the overall ventilation is needed in e.g. hospitals. This again allows a shorter distance between two storeys.

Method

An aspect of the invention relates to a method for partly isolating an area/room and/or removing microorganisms and/or viruses and or health-hazardous matter in air from an area/room, where the method comprises Localising an area which is to be at least partly isolated,
Obtaining at least one filtration/ventilation unit as described herein,
Establishing a filtration/ventilation system as described elsewhere herein around or in connection to the area,
Directing air from the surrounded area/room into the at least one filtration/ventilation unit,
Directing air out of the at least one filtration/ventilation unit in a direction of between 0° to 90° when compared to the overall or central direction of air being directed into the filtration/ventilation unit and/or directing air out of the at least one filtration/ventilation unit and further into pipes or openings in e.g. the ceiling directing the air to a larger ventilation system, hereby
Partly isolating the area and/or removing microorganisms and/or viruses and/or health-hazardous matter in air from the area.

The filtration/ventilation units and/or filtration/ventilation system described together with the method may comprise filtration/ventilation units with any features described elsewhere herein and any combination of the described features.

In a preferred embodiment the localised area is an indoor area. Preferred areas can be realised from the preferred uses of the filtration/ventilation unit described herein. Most preferably the area is an area to be occupied by persons/object being at risk of spreading air-borne diseases or contaminants and/or an area to be occupied by a person/object to be isolated from a risk of obtaining an airborne disease or contaminant intoxication.

The method may thus be used to reducing spread of microorganisms and airborne health hazardous matter from a surrounded area and/or for protecting the surrounded area from microorganisms and airborne health hazardous matter which may be present in the room air outside of the surrounded area.

One way to control the dispersion of coughed air is to exhaust this air locally i.e. close to the mouth of the individual e.g. a diseased person. Close to a coughing individual the coughing jet is still less mixed with the surrounding air. It is preferred to locate the filtration/ventilation unit as described herein with the first air slot being located towards the individual such that the distance from the air source e.g. the mouth and nose to the first air slot is below 1 m, such as below 90 cm, e.g. below 80 cm, such as below 70 cm, e.g. below 60 cm, such as below 50 cm, e.g. below 40 cm, such as below of 30 cm, e.g. below 20 cm. Preferably the distance from the air source to the first air slot of the filtration/ventilation unit is between about 10 cm to about 60 cm, more preferred between about 15 cm to about 55 cm, further preferred between about 20 cm to about 50 cm, yet further preferred between about 20 cm to about 45 cm, even further preferred between about 20 cm to about 40 cm, most preferred between about 20 cm to about 35 cm. A short distance increases the possibility of the filtration/ventilation unit to catch the air from the air source and thus to catch air borne infectious agents. Preferably, the distance from a patients head to the filtration/ventilation unit is from 0.2 m to 0.6 m assuming a maximal bed width of 1 m.

In a hospital room infectious people spend most of the time lying in their bed. This is especially true during the symptomatic stage of the disease when individuals are highly contagious. Examples of such situations can be airborne contagious diseases like measles, small pox, tuberculosis etc. The use of a filtration/ventilation unit as described herein in close proximity to the head of the diseased person improves a successful evacuation of at least the largest part of the pathogen laden air from pulmonary activities. The air can be purged (e.g. via UVGI) and directed e.g. upwards at elevated velocities, through one or more horizontal slots of the ventilation/filtration unit, towards an exhaust vent of the total volume ventilation. The clean air directed upwards can act as a barrier between an individual e.g. a medical staff member staying close to the bed in which a patient is lying. Furthermore the discharged air jets (acting as air curtains) will entrain the coughed air and move it upward directing it towards the exhaust.

The method may also be used in any other situations described herein, especially the situations described in respect of use of the filtration/ventilation unit.

A Hospital Bed Integrated Cleaning Unit

An embodiment of the invention relates to a bed with at least one filtration/ventilation unit as described elsewhere herein located at least at the head region of the bed, where the at least one filtration/ventilation unit can be an integrated part of the bed or the at least one filtration/ventilation unit can be mounted on the bed such that the at least one filtration/ventilation unit can be repositioned together with the bed. The bed may be denoted a hospital bed, however, such a bed can be used in other locations than in hospitals. Examples of locations are mentioned elsewhere herein.

A number of filtration/ventilation units may be attached to a bed to establish a filtration system around the mattress of a bed. The system may comprise at least two filtration/ventilation units and the filtration/ventilations units can be located with at least one filtration/ventilation unit at each side of the head region of the bed.

The bed may further comprise a filtration/ventilation unit at least one end of the bed. If positioned at the head end of the bed, the bed may have one filtration/ventilation unit at each side of the head of a patient lying in the bed as well as behind the head of the patient. If positioned at the foot of bed, the bed may have one filtration/ventilation unit at each side of the head of a patient lying in the bed as well as at the feet of the patient. Also a filtration/ventilation unit may be positioned at each side of the head of the patient, behind the patients head and at the feet of the patient.

Figure 8:
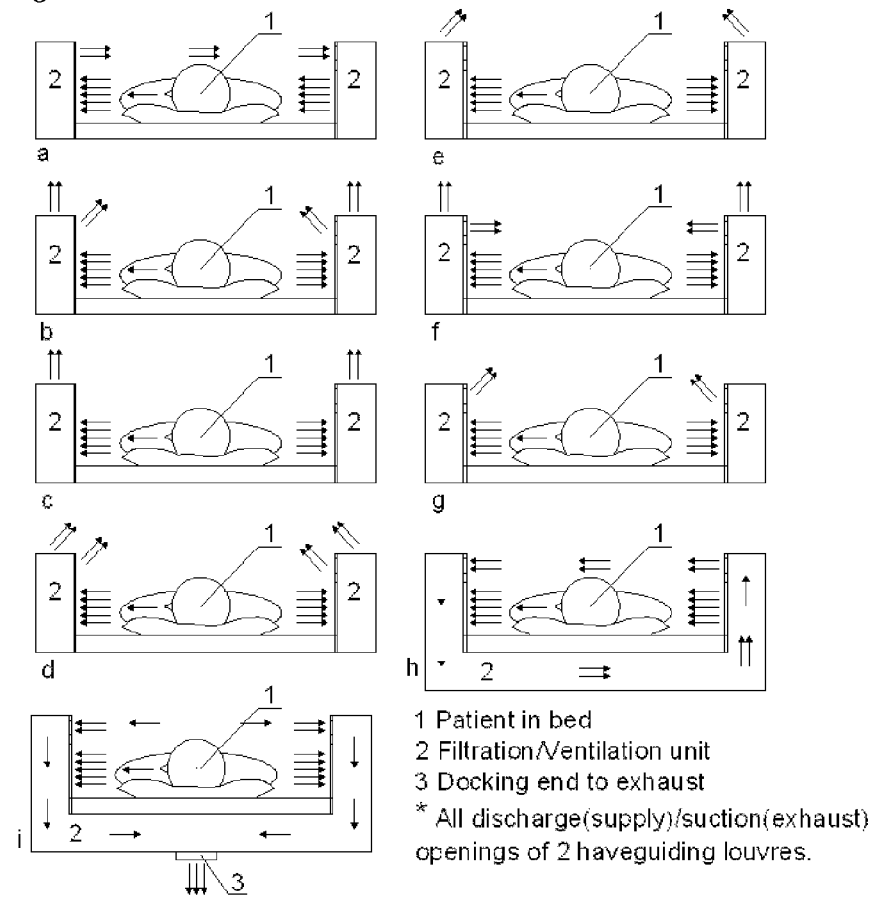
FIG. 8 Some possibilities for air distribution control strategies around a patient lying in a bed with a filtration/ventilation unit positioned at each side of the head.

The cabinet of a filtration/ventilation unit for a hospital bed may be shaped as a box with dimensions of e.g. 0.6 m×0.15 m×0.62 m (length×width×depth/height). The unit can be installed at the sides and/or head of a hospital bed. As described elsewhere the filtration/ventilation unit can help to exhaust the air from the pulmonary activities of the diseased occupant/patient (breathing, coughing, sneezing etc.), the unit cleans the air by removing/killing the pathogens via a filter and UVC light and then the air is discharged substantially vertically (or in other directions e.g. as indicated in FIG. 8) through one or more air outlet slot. The air leaving the filtration/ventilation unit has a high initial velocity and direction towards the ceiling where the air can be exhausted by the total volume ventilation (background ventilation). The air inlet slots may be two slots made on the device (0.50 m×0.14 m, L×W), one on each side of the box, and a discharge opening (0.54 m×0.05 m, L×W) on the top as indicated in FIG. 18. In some situations the air inlet slot(s) can be used as air outlet slot(s) and the air inlet slot(s) can be used as air outlet slot(s). These applications claimed in the above mentioned patent application were not studied due to the limited time. The filtration/ventilation unit as shown in FIG. 18 can be designed to have two different sections separated from each other by a firm partition, hereby one section is used for supply of clean air and the other section is for exhaust of diseased or potentially diseased air. The partition may be positioned diagonally between two corners of the interior of the filtration/ventilation unit.

The filtration/ventilation units can be attached to the bed with fastening means such as a hinge or a track allowing the filtration/ventilation unit to be removed entirely from the bed and/or to be tilted/glided about 180° downward in vertical direction. The fastening means may also be of a type allowing adjustment of the unit in the direction up/down and/or forward/backward. The removal or tilting/gliding away of a filtration/ventilation unit may give e.g. a staff at a hospital improved space to handle the patient. An automatic controlling unit may turn off the filtration/ventilation unit if the unit is tilted and/or the height of the inlet can be changed by sliding latch and/or an automatic controlling unit may adjust the output slots to obtain a proper direction of cleansed output air.

The bed whereon filtration/ventilation unit could be attached may be any kind of beds e.g. a bed for prolonged rest of a human such as hospital bed, caring bed, bed at nursing home, care home, at old people's home, commercially available beds for home application etc.

The bed suitable for positioning a filtration/ventilation system as described herein with one, two, three or more filtration/ventilation units as described elsewhere herein is a bed for a single user. However, on a double bed filtration/ventilation units may be positioned at each side of the head region and at the end of the bed at the head region.

The bed to be used for filtration/ventilation units as described herein is preferably about 2 m long and about 1 m broad. However, for children the size can be smaller, and for overweight persons or long persons the size can be larger.

The bed as described herein may comprise a filtration/ventilation unit with any of the features described elsewhere herein, among these features are:

The filtration/ventilation unit comprises at least one means for killing or inhibiting the growth capability of microorganisms or virus such as a filter for filtration of air directed through the filtration/ventilation unit, the filtration/ventilation unit comprises at least one air outlet for directing air out of the filtration/ventilation unit, the air outlet may have a smaller dimension than the air inlet and/or means for controlling the direction of the outlet air and/or means for controlling the velocity of the outlet air, the filtration/ventilation unit comprises at least one air inlet for directing air into the filtration/ventilation unit and/or the filtration/ventilation unit comprises at least one fan for direction air through the filtration/ventilation unit the filtration/ventilation unit is capable of producing at least one air curtain with the features as described elsewhere herein.

The filtration/ventilation unit may also comprise the filtration/ventilation unit comprises at least one means capable of emitting electromagnetic waves such as a light bulb capable of emitting light having a disinfecting effect on microorganisms present in the air directed through the filtration/ventilation unit.

Figure 7:
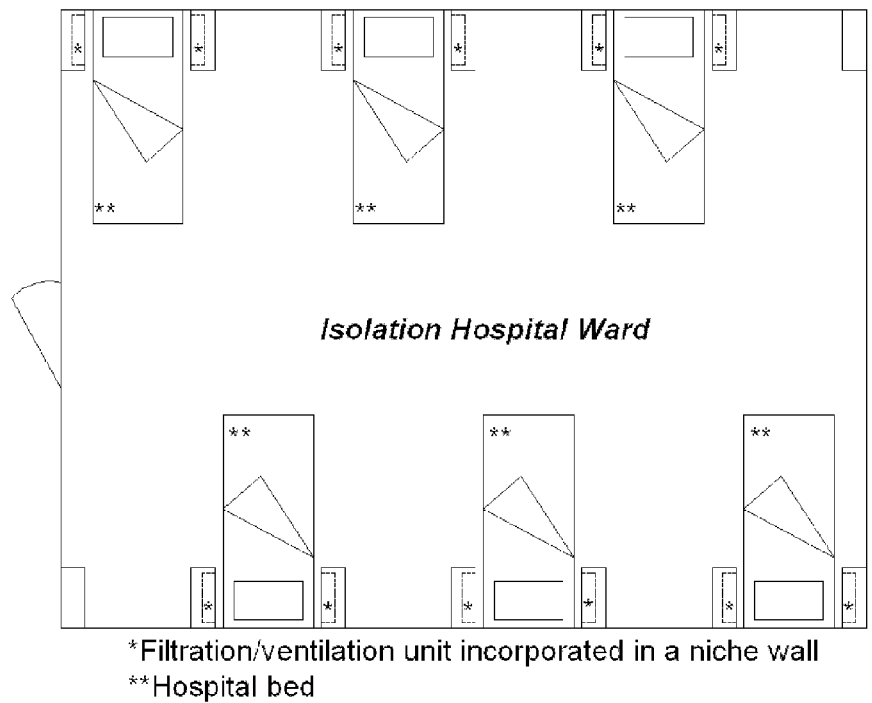
FIG. 7 Overview of an isolation hospital ward with filtration/ventilation units (boxes) installed in "partition walls" at the part of the beds where the head of the patient will be located.

The filtration/ventilation unit could also be integrated into the walls or small niches in the walls and the bed could be docked there. In this way the boxes exhaust the air directly to the total volume ventilation exhaust and/or may produce a substantially vertical air curtain. A room with small niches for beds is illustrated in FIG. 7.

The filtration/ventilation unit of the bed can have infrared temperature sensor allowing for identification of the position of the face of a lying person (i.e. head directed left, right or upwards) and thus activating the needed side board unit (filtration/ventilation unit). This would imply energy efficiency and a good performance of the described system. Other sensors as described herein may also be a part of the filtration/ventilation unit.

Another modification of the filtration/ventilation unit system is with one unit installed in the rear board, behind the head and one unit at each side of the head. In this case air can be sucked continuous from e.g. the two side boards or can be automatically controlled to suck the air through the opening the patient is facing currently. In this case and in other arrangements/systems as well, an automatic control of the velocity of the air of the inlet air (suction strength) and outlet air may be performed and be depending on the activity and thus exhalation activity and/or frequency of cough as well as position of the patients head. The unit could be made with a velocity detection sensor so as when the patient coughs the amount of inlet air (suction strength) and amount of outlet air is increased to the maximum to allow for faster evacuation and better effectiveness at capturing the released pathogens.

It is also possible to use only one cleaning section installed in the back board (filtration/ventilation unit located behind the head of a patient) as well as one air discharge slot placed on the top of the back board. This may simplify the design of the unit and may provide a good aesthetic design. This modification may also be less disturbing for medical manipulation procedures.

The size and the shape of the unit should allow for lifting part of the bed, i.e. the section below the upper part of the body, when a patient is resting. In this case louvers/lamellas/slats placed in the discharge slots will be activated automatically (mechanical mechanism or other) to discharge the air vertically.

The filtration/ventilation unit could be made attached firmly to the wall of the insulation room allowing for the hospital bed to be docked or dislocated easily from it as to offer easy transportation of the patient as needed. Also a portable version of the filtration/ventilation unit could be produced with rechargeable batteries to ensure transportation of infectious patients between wards in the hospital, or e.g. from an ambulance and to a hospital ward.

Apart of providing efficient protection to people from cross-infection and improving their quality of life (reducing psychological stress), this invention has a great potential for lowering energy consumption in hospital wards. Energy savings could be as high as doubled due to reduced airflow rates of the background ventilation system. Another reason for the energy reduction is due to the fact that the filtration/ventilation unit also purges the airborne pathogens and therefore recirculation could be applied for the running total volume system.

Normally, in hospitals persons diseased with an air-borne disease are located in rooms with only one or two patients. However, in epidemic or pandemic situations the hospitals may be in deficiency with rooms for one or two patients. In such situations the beds in larger rooms may be mounted with filtration/ventilation units as described herein to isolate the patients from each other by the air curtains produced by the filtration/ventilation units. Hereby the hospital staff as well as visitors are also protected from the air-borne disease by the air curtains.

Use of Filtration/Ventilation Unit

An aspect of the invention relates to use of a filtration/ventilation unit and/or a filtration/ventilation system as described herein.

Examples of use of the unit and/or system can be e.g.:

At beds at hospitals, nursery, premature, newborn babies, kids, post operation rooms, rooms for waking up following an operation, when replacing bandage, in over-pressurised rooms for treatment of immuno-compromised patients or patients with extensive body burns etc.

The beds at hospitals may be any beds, or it may be beds for patients having an airborne disease; beds for patients subjected to a transplantation e.g. liver or heart transplantation; beds for patients having HIV or AIDS; beds for patients with an influenza e.g. avian influenza, swine influenza (e.g. H1N1), Severe Acute Respiratory Syndrome (SARS).

At beds: home, in ambulance.

Day care centre e.g. in sleeping rooms

In aeroplanes, busses, trains and other transport means in seats in front of a passenger, in the walls, hanging down from the ceiling, in the seats producing an air curtain towards the corridor and/or between passengers.

In children's playground spaces or nursery centres such as playgrounds in day care centres or nurseries, in shops etc.

In offices e.g. on tables and/or mounted onto a computer screen. A filtration/ventilation unit aspirating air at the region above a computer screen and blowing the air vertically at the ends of the table or blowing the air horizontally from the region besides the computer screen.

Integrated in computer screens where air can be aspirated at the top of the computer screen and blown out at the side of the computer screen. The size and weight of the filtration/ventilation unit may be smaller that described in respect of a cabinet suitable to connect e.g. to a bed.

Mobile use i.e. the filtration/ventilation unit can be placed where desired and be moved to other locations e.g. at home, at offices, at hospitals. The mobile units can be portable and working based on an internal battery and/or can be connected to the mains. Mobile units may also have wheels and a battery and/or means to be connected to the mains.

In public (airplane, train, bus, ship) toilets or connected to toilets other places e.g. in hospitals, day care centres, retirement home at both sides of the toilet seat incorporated into the toilet walls or located besides the toilet.

Figure 16:
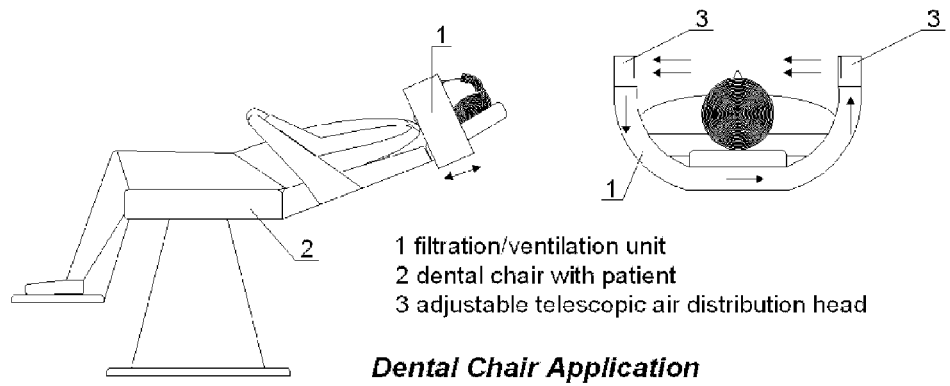
FIG. 16 A dental chair application. In this case the end of the device can be made telescopic to be adjustable depending on the patient.

In dental clinics (an example of a dental chair application is given in FIG. 16). In this case the end of the device can be made telescopic to be adjustable depending on the patient.

In animal houses e.g. in stables to minimising the risk of microorganisms, viruses or any other health hazardous airborne matter to dissipate from one animal to other animals and/or from one group of animals to other groups of animals and/or from one or more animals to humans. The filtration/ventilation units may be located between sties with animals and/or between a sty and the feed alley or another area used by humans handling the animals. The direction of the cleansed air may e.g. be horizontal, upward vertical or the air may be directed out of the stable e.g. through a ventilation system.

The filtration/ventilation units or system can also be used in other locations where animals live e.g. veterinary hospitals, zoos, kennels, catteries etc. A filtration/ventilation system as described elsewhere herein may be installed around the areas for one or more animals e.g. a cage. In the text describing a hospital bed, these situations may be replaced with the systems described for animals e.g. sties, cages.

To surround dead individuals e.g. dead animals or dead people. The surrounding (partly or complete surrounding) can be performed at any stage of handling the dead individuals.

In temporary hospitals or temporary sections of a hospital. Temporary hospitals may e.g. be military hospitals, hospitals set up in areas subjected to disaster. In such hospitals, the ventilation/filtration units as described herein may be the only possibility to isolate persons if only a limited or no isolations rooms are present.

In ambulances to create an air curtain between the patient and the staff.

To be used in food and beverage industries to protect the food and beverage from contamination when the food is being packed and when the beverage is entered into the packaging/bottle, when the beverage is directed towards the locations for mounting a lid or the like on the packaging/bottle. Filtration/ventilation units can be located at each side of a transport belt for transportation of the food or beverage products. The filtration/ventilation unit can thus be located next to a transport belt or can be an integrated part of a food/beverage transportation belt. Especially the filtration/ventilation unit can be used in connection to or be an integrated part of a transportation belt where the food or beverage are not sealed and there is a risk of food contamination and poisoning.

In pharmaceutical industry similar to the food and beverage industry application. Implemented in the production cycle of vaccines and pills that require clean environment and special conditions for filling and handling when regarding their contamination via the airborne route.

In electronic and computer industry for clean room manufacture of electronic parts.

To remove flavours or smell e.g. to remove smell of food in kitchens or any other smell polluting productions (tanneries etc). Air can be aspirated from the area out of the area where preparing food/handling the product producing smell where the air enters at least one ventilation/filtration unit as described herein and the air can be directed towards the ceiling to produce an air curtain decreasing the risk of entrance of micro organisms into the cooking area and sealing the space from smell transfer.

Some of the benefits when using the unit and/or system can be:

Improved protection for medical staff and patients,
Reduced risk from airborne and nosocomial infections due to leakages and malfunctions in the total volume ventilation in hospitals,
Improvement of human well being,
Reduced energy consumptions,
Reduced initial investment costs (e.g. more than one occupant in an isolation room),
Lower maintenance costs.

REFERENCES

ASHRAE. 2004. ANSI/AHRAE Standard 55-2004. Thermal environmental conditions for human occupancy. American Society of Heating. Refrigerating and Air-Conditioning Engineers. Inc.

ASHRAE Handbook 2007, HVAC Application, SI Edition, Chapter 7—Health Care Facilities. American Society of Heating, Refrigerating and Air-Conditioning Engineers, Inc., Atlanta, USA.

ASHRAE. ANSI/ASHRAE/ASHE Standard 170-2008. Ventilation of Health Care Facilities. American Society of Heating, Refrigerating and Air-Conditioning Engineers, Inc., Atlanta, USA.

Awbi H., 2003, Ventilation of Buildings, Second edition, ISBN 0-415-27056-1, Spon Press 2003.

CEN CR 1752, 1998. Ventilation for Buildings: Design Criteria for the Indoor Environment.

DS 2451-9, Styring af infektionshygiejne i sundhedssektoren—Del 9: Krav til indkøb og vedligehold af teknisk og medicinsk-teknisk udstyr, Dansk Standard—Danish Standards Association, 2003-04-30.

European Standard 2007. EN 15251 2007. Indoor environmental input parameters for design and assessment of energy performance of buildings addressing indoor air quality. thermal environment. lighting and acoustics. EUROPEAN COMMITTEE FOR STANDARDIZATION. B-1050 Brussels.

Hyldgaard. C. E. 1994. Humans as a source of heat and air pollution. In: Proc. ROOMVENT '94. 4th Int. Conf. on Air Distribution in Rooms. Krakow. Poland. pp. 414-433.

ISIAQ Review on Indoor Air Quality in Hospitals and Other Health Care Facilities, October 2003.

Launder, B. E. and Spalding D. B. (1974) "The numerical computation of turbulent flows", Computer Methods in Applied Mechanics and Energy, 3, 269-289.

Melikov, A. K., 2004, Breathing thermal manikins for indoor environment assessment: important characteristics and requirements, European Journal of Applied Physiology, vol. 92, number 6, September 2004, pp. 710-713.

Melikov. A. K. and Kaczmarczyk. J., Indoor air quality assessment by a breathing thermal manikin, 2007, Indoor Air 17 (1). pp. 50-59.

Patankar, S. V. (1980) "Numerical heat transfer and fluid flow", New York, Hemisphere Publishing Corp.

World Health Organization, Guidelines on Prevention and Control of Hospital Associated Infections, January 2002, SEA-HLM-343.

DETAILED DESCRIPTION OF THE DRAWINGS

FIG. 1 illustrates an embodiment of the filtration/ventilation unit. Exhalation air from a patient enters the filtration/ventilation unit at the side of the unit due to a negative pressure produced by the fan (1). The air is directed through means (2) for killing or inhibiting the growth capability of microorganisms or virus e.g. a filter, here illustrated by a HEPA filter. The air passes means (3) capable of emitting electromagnetic waves e.g. lights emitting Ultra Violet light, here illustrated by Ultraviolet germicidal irradiation (UVGI). A straightener (4) or stabilisator is positioned to secure the shape of the unit. Guiding veins (5) guides the outlet air in a specific direction, here illustrated by straight upward direction. Damper (6) may adjust the amount of air entering or leaving a slot of the unit. A docking (7) may be used to connect the filtration/ventilation unit to an exhaust system or to the outside of a building as shown in FIG. 3, possibility 4.

Figure 2:
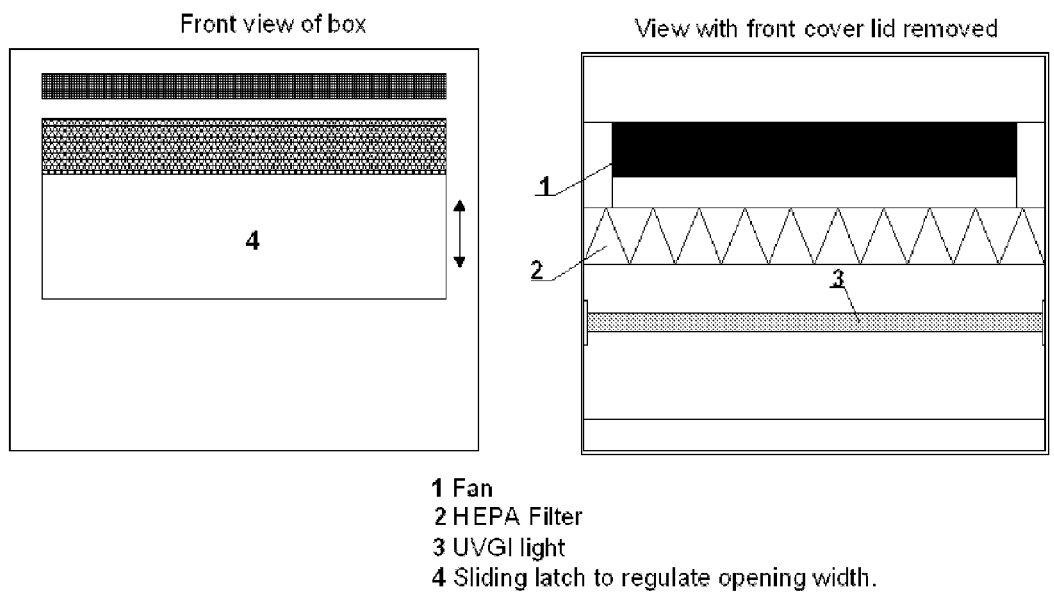
FIG. 2 Front view of a filtration/ventilation unit and a front view with the cover lid removed.

FIG. 2 Front view of the filtration/ventilation unit and a front view with the cover lid removed. A fan (1) directs air through the unit. Means (2) for killing or inhibiting the growth capability of microorganisms or virus, e.g. a HEPA filter filtrate the air. Means (3) capable of emitting electromagnetic waves e.g. a UVGI light also participate in the elimination of the harmful organisms or particles.

Figure 3:
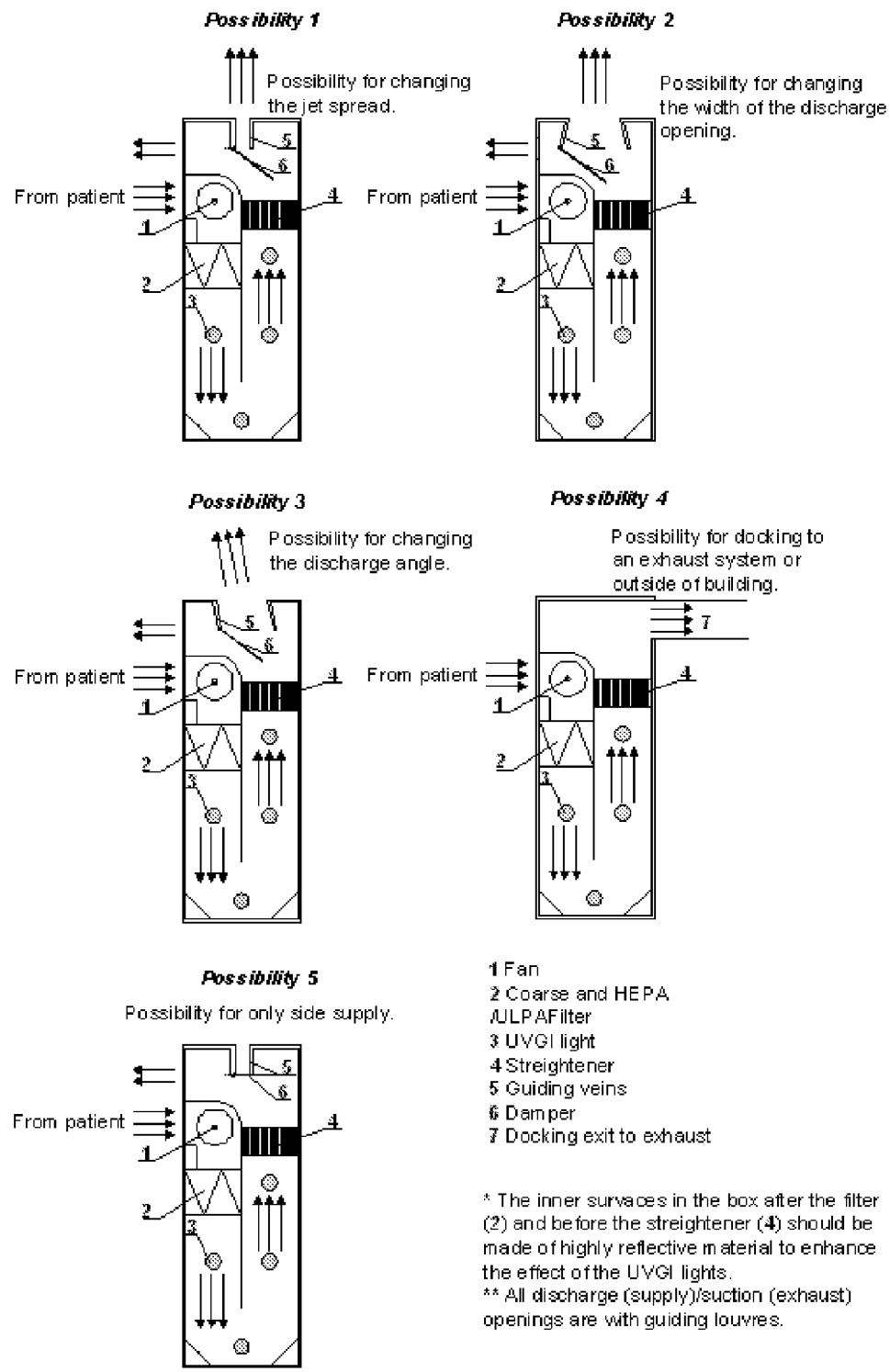
FIG. 3 Different possibilities for the direction and connection of the outlet air directed from the filtration/ventilation unit.

FIG. 3 illustrates different possibilities for the direction of the outlet air discharged from the filtration/ventilation unit. In possibility 1, the air is directed straight upward with a possibility for changing the jet spread. Possibility 2 shows that it is possible to change the width of the discharge opening. Possibility 3 shows that it is possible to change the discharge angle. In Possibility 4 the exhaust air is directed to an exhaust system or to the outside of the building/room and used to recirculate back in the room.

FIG. 4 illustrates a schematic presentation of a hospital room with: a) Mixing ventilation alone with two air outlets and one air inlet positioned in the ceiling, b) Mixing ventilation with the cleaning (filtration) unit installed in cabinets at the head of the patients. In this example the cleaning (filtration) unit in the bed at the left has a suction slot directed towards the patient and a horizontal slot for outlet air. The bed in b) has can have a filtration/ventilation unit as described elsewhere herein in both of the side panels as well as in the panel at the end of the bed (behind the head of the individual). It is also possible only to have the two side panels with the filtration/ventilation unit as described herein and no panel at the end of the bed. A panel may be the filtration/ventilation unit itself.

FIG. 5 illustrates computer simulations (CFD) of distribution of air coughed by one patient directed towards a patient in another bed and in a room (illustrated in FIG. 4a) with mixing ventilation alone at 12 ACH (air-changes per hour), minimum ventilation requirement for infectious wards.

FIG. 6 illustrates computer simulations (CFD) of distribution of air coughed by one patient directed towards another patient and in a room (illustrated in FIG. 4a) with beds each with two filtration/ventilation units installed at the head of the patients and with mixing ventilation at 6 ACH (air-changes per hour).

FIG. 7 Overview of an isolation hospital ward illustrated with 6 beds and the cleansing boxes incorporated in niche walls. The cleansing boxes could also be mounted directly at the beds as described elsewhere herein.

FIG. 8 Some possibilities for air discharge directions around the head of a patient with a cleansing unit located at each side of the head. In situation a) air is directed towards the back of the head and exhausted from the front of the head and at the same time a horizontally air curtain is produced above the head of the patient. This situation may be combined with a vertical air curtain and/or a diagonal air curtain as also illustrated in situation d), e) or g). In situation b) air is exhausted from both sides of the head of the patient and the air is directed out from the cleansing units vertically and upwardly although in a diagonal line of air streams. In situation c) air is exhausted from both sides of the head of the patient and the air is directed out from the cleansing units vertically producing vertical air curtains on both sides of the head of the patient. In situation d) air is exhausted from both sides of the head of the patient and the air is directed out from the cleansing units upwardly although in a diagonal line of air streams. The air is directed out of the cleansing unit from the top of the boxes. In situation e) air is exhausted from both sides of the head of the patient and the air is directed out from the cleansing units vertically and horizontally towards each other above the head of the lying patient. In situation f) air is exhausted from both sides of the head of the patient and the air is directed out from the cleansing units upwardly although in a diagonal line of air streams. The air is directed out of the cleansing unit from the upper part of the side of the boxes facing the head of the patient. In situation g) air is exhausted from both sides of the head of the patient and the air is directed out from the cleansing units upwardly although in diagonal lines of air streams. The air is directed out of the cleansing unit from the top of the boxes and from the upper part of the side of the boxes facing the head of the patient. In situation h) two filtration/ventilation bed-attached units are connected to generate recirculation air flow. In situation i) installation when two bed-attached units can be connected to the exhaust of the background ventilation system. The Figure only illustrates some of the possibilities in respect of exhausting air from a patient and directing the air out of the filtration/ventilation unit, other possibilities in respect of the air directions into and out of the filtration/ventilation unit also exists.

Figure 9:
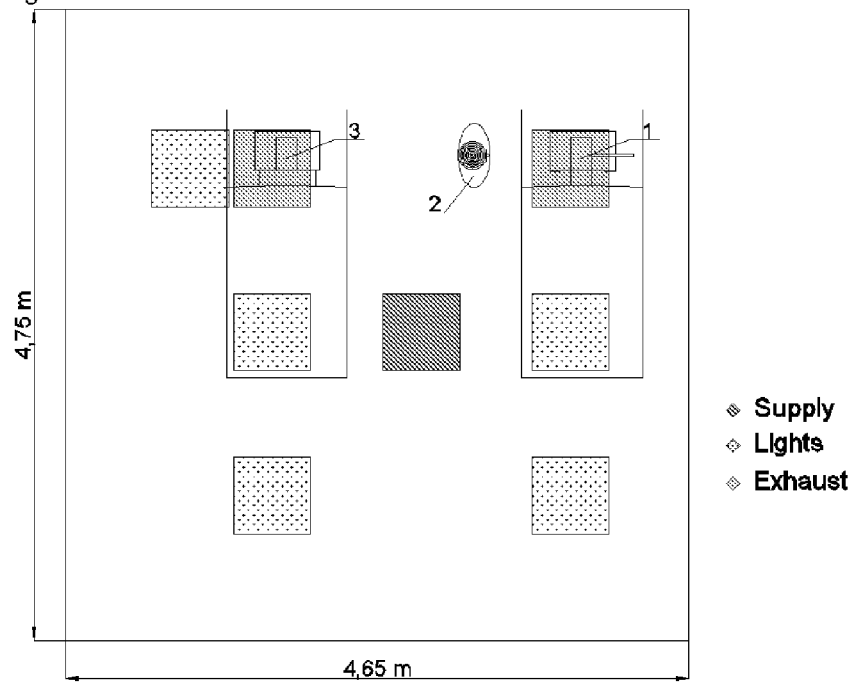
FIG. 9 Set up of beds during experiment.

FIG. 9 Set up of beds during experiment. The figure is further described in Example 2.

Figure 10:
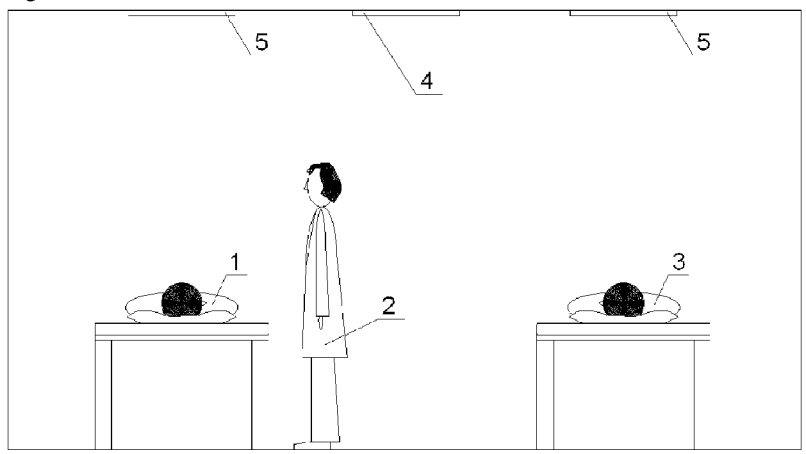
FIG. 10 Set up of beds during experiment, with a patient in each bed and a doctor between the two beads. No cleansing devise (filtration/ventilation unit) is present.

FIG. 10 Set up of beds during experiment, with two patients and a doctor. No cleansing devise (filtration/ventilation unit) is present. The figure is further described in Example 2.

Figure 11:
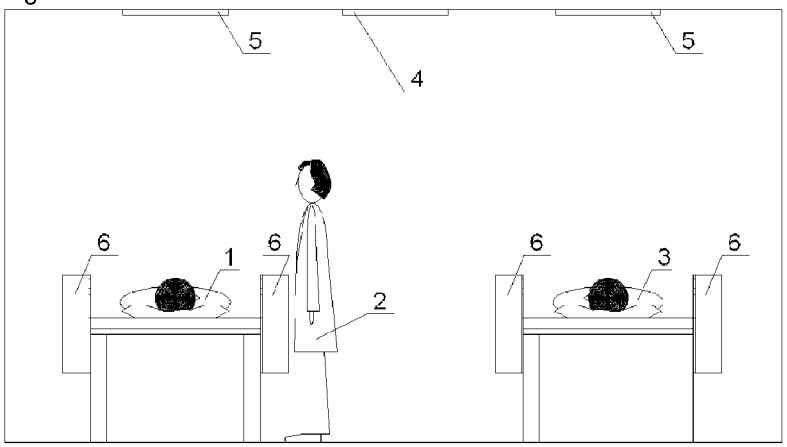
FIG. 11 Set up of beds during experiment, with a patient in each bed and a doctor between the two beads. Cleansing devises (filtration/ventilation units) are present next to the head of the patients.

FIG. 11 Set up of beds during experiment, with two patients and a doctor. Cleansing devises (filtration/ventilation units) are present next to the head of the patients. The figure is further described in Example 2.

Figure 12:
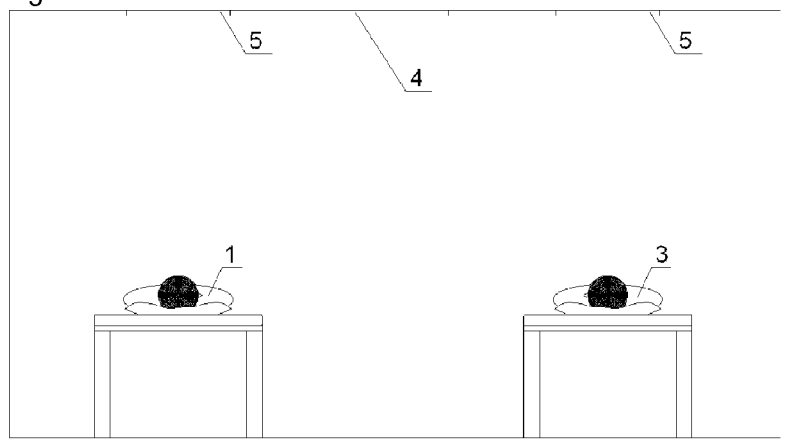
FIG. 12 Set up of beds during experiment, with a patient in each bed. No cleansing devise (filtration/ventilation unit) is present.

FIG. 12 Set up of beds during experiment, with two patients. No cleansing devise (filtration/ventilation unit) is present. The figure is further described in Example 2.

Figure 13:
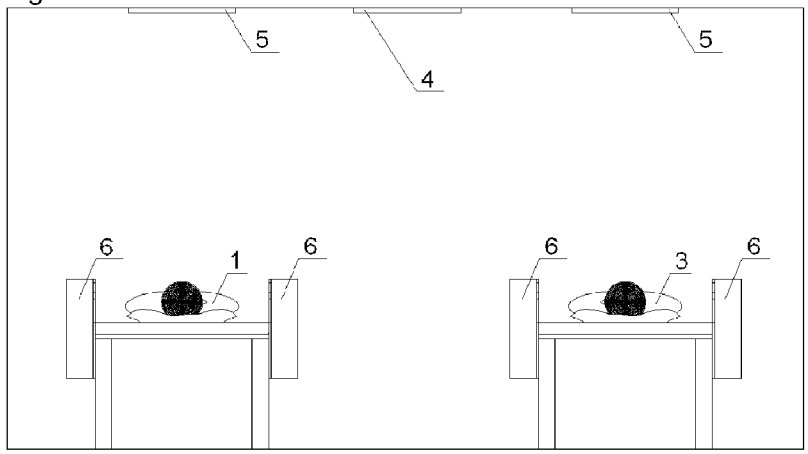
FIG. 13 Set up of beds during experiment, with a patient in each bed. Cleansing devises (filtration/ventilation units) are present next to the head of the patients.

FIG. 13 Set up of beds during experiment, with two patients. Cleansing devises (filtration/ventilation units) are present next to the head of the patients. The figure is further described in Example 2.

Figure 14:
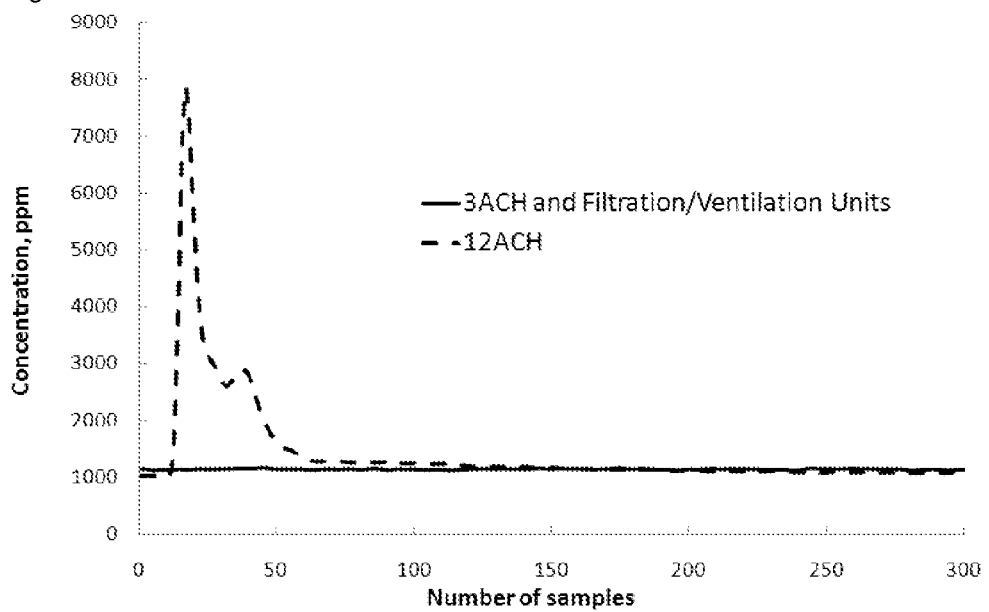
FIG. 14 Exposure of the doctor (in FIGS. 10 and 11) to coughed pathogen laden air with and without cleansing devises present at the head of the patients.

FIG. 14 Exposure of the doctor (in FIGS. 10 and 11) to coughed pathogen laden air with and without cleansing devises present at the head of the patients. The Figure illustrates the Concentration at the mouth of the doctor, resembled by a thermal manikin when standing by the bed with and without the bed integrated cleansing unit. The thermal manikin is facing the opening of the coughing machine integrated with a heated dummy simulating sick person lying in the bed. The results are further described in Example 2.

Figure 15:
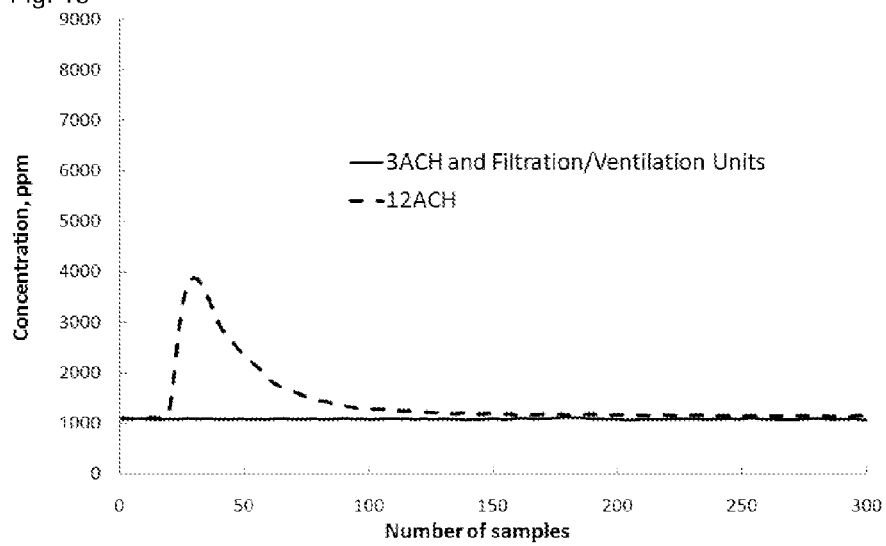
FIG. 15 Exposure of one of the patients (in FIGS. 12 and 13) to coughed pathogen laden air with and without cleansing devises present at the head of the patients.

FIG. 15 Exposure of one of the patients (in FIGS. 12 and 13) to coughed pathogen laden air with and without cleansing devises present at the head of the patients. The Figure illustrates the concentration of $CO_2$ at the mouth of the thermal manikin which simulates a patient in the bed beside the bed of a coughing patient. Results obtained with and without bed integrated cleansing unit. The thermal manikin is facing the opening of the coughing machine integrated with a heated dummy simulating sick person lying in the bed. The results are further described in Example 2.

FIG. 16 A dental chair application. A filtration/ventilation unit (1) is located around the head of the individual/patient sitting in the chair (2). Distribution heads (3) are located on both sides of the head of the patient to allow an air stream to be produced above the head of the sitting/lying patient i.e. one distribution head is used for aspirating air, the other distribution head is used for the output of cleansed air. The air is cleansed in the tube located around the chair. The tube may have means for killing or inhibiting the growth capability of microorganisms or virus present in and means capable of emitting electromagnetic waves at a wave length having a disinfecting effect on microorganisms or viruses as described elsewhere herein. The direction of the air stream may be reversed. The end of the device at the distribution heads (3) can be made telescopic to be adjustable depending on the size of the patient.

FIG. 17 illustrates the outer dimensions of a filtration/ventilation unit. The following dimensions are examples for an embodiment of the filtration/ventilation unit as described herein: length: 60 cm; height 60 cm, width 14.5 cm. The first air slot i.e. the slot at the suction side is shown to have a length of 50 cm and a height of 13.5 cm. The lowest part of the first air slot is positioned 19.5 cm from the top of the box (the filtration/ventilation unit). The second sir slot is shown to be 53.5 cm long and 5 cm in width. However, other dimensions of the box and the air slots are possible. Also other locations and numbers of air slots are possible.

FIG. 18 illustrates a bed with a filtration/ventilation unit at each side of the head of the individual (patient) lying in the bed. In this example an air curtain (discharged air towards ceiling) is made from a clean air supply, whereas the air entering the filtration/ventilation unit(s) is led to an exhaust system and thus removing the air from the room/location. The amount of air let to the exhaust system by a filtration/ventilation unit is indicated to the similar to the amount of clean air being directed into the filtration/ventilation unit to produce the air curtain. Any of the situations a to h shown in FIG. 8 may be combined with the situation shown in FIG. 18. In such situations the air producing the air curtain is preferably clean air from an external supply and the air entering the filtration/ventilation unit through a second air slot is led to an exhaust system and removed from the room/location through ventilation channels or tubes.

FIG. 19 illustrates air distribution in a room with a filtration/ventilation unit as a Hospital Bed Integrated Ventilation Cleansing Unit (HBIVCU) (5). Sick patients (1 and 3) are lying in the beds and are coughing or breathing upwards towards exhaust (4) of total volume ventilation. An individual e.g. a doctor (2) is sealed/protected within the clean zone by the air curtains created by the HBIVCU (5). The arrows indicate the direction of air. The filtration/ventilation units may be as described elsewhere herein.

Figure 20:
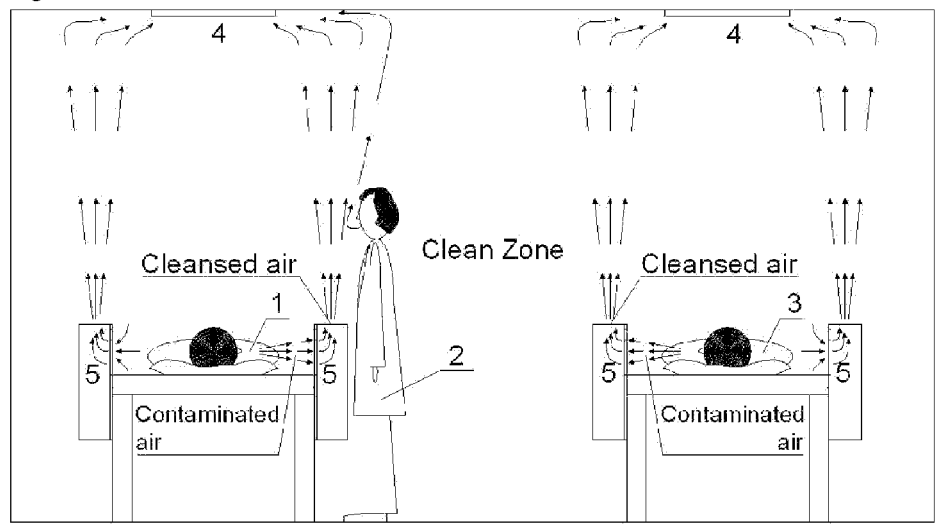
FIG. 20 A room with a filtration/ventilation unit where sick patients are lying in the beds and are coughing or breathing sideways.

FIG. 20 illustrates air distribution in a room with a filtration/ventilation unit as a (Hospital Bed Integrated Ventilation Cleansing Unit (HBIVCU) (5). Sick patients (1 and 3) are lying in the beds and are coughing or breathing sideways. An individual e.g. a doctor (2) is sealed/protected within the clean zone by the air curtains created by the HBIVCU (5). The contaminated air is cleansed and directed upwards towards the ceiling to the total volume ventilation exhaust (4). The arrows indicate the direction of air. The filtration/ventilation units may be as described elsewhere herein.

Figure 21:
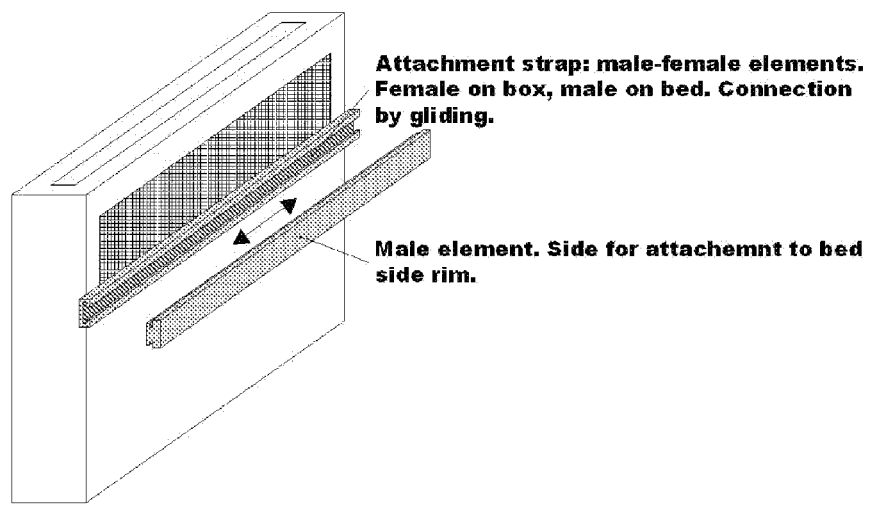
FIG. 21 An attachment strap of a filtration/ventilation unit.

FIG. 21 illustrates a possible way of attaching the filtration/ventilation unit/box as described elsewhere herein to a bed e.g. to a patients' beds. An attachment strap (attachment means) as male-female elements is illustrated. Female element is illustrated on the box, male element is illustrated on the bed side rim, however, the opposite is also possible. The connection is performed by gliding. Other fastening means are also possible.

Figure 22:
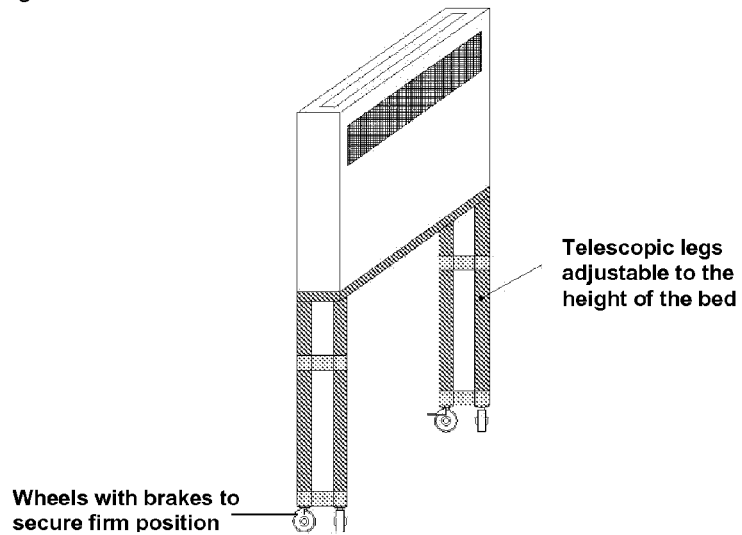
FIG. 22 A filtration/ventilation unit with wheels and legs.

FIG. 22 illustrates a filtration-ventilation unit placed on stand with wheels and legs. The wheels may be with brakes to secure firm position and the legs may be telescopic to adjust the inlet area of the box to the height of the hospital bed or to adjust the height in respect of another situation e.g. when an individual sits in a chair.

Figure 23:
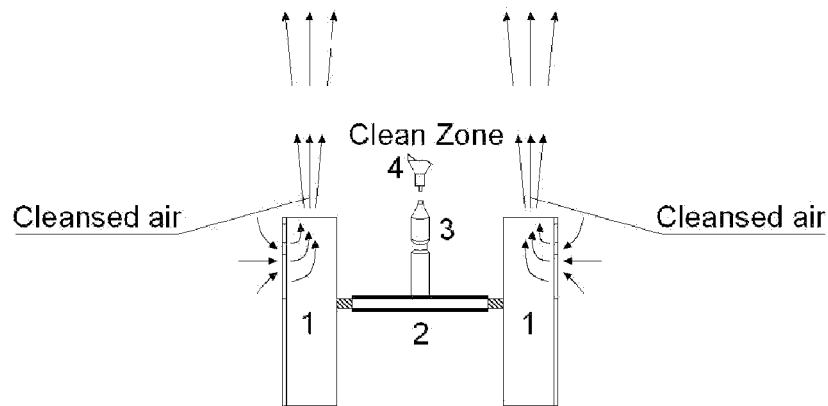
FIG. 23 Use of filtration/ventilation units in the food and beverage industry.

FIG. 23 illustrates an application of the filtration/ventilation unit in the food and beverage industry. The filtration/ventilation unit (1) is equipped on both sides of a conveyor belt (2), which transports the bottles or packaging/container for food or beverage. The filtration/ventilation units (1) can create a clear/cleansed zone around the beverage/food container (3) before these are filled by the beverage or food, while these are filled by food or beverage through an injector (4), and/or at least until the bottles/containers/packings are closed.

Figure 24:
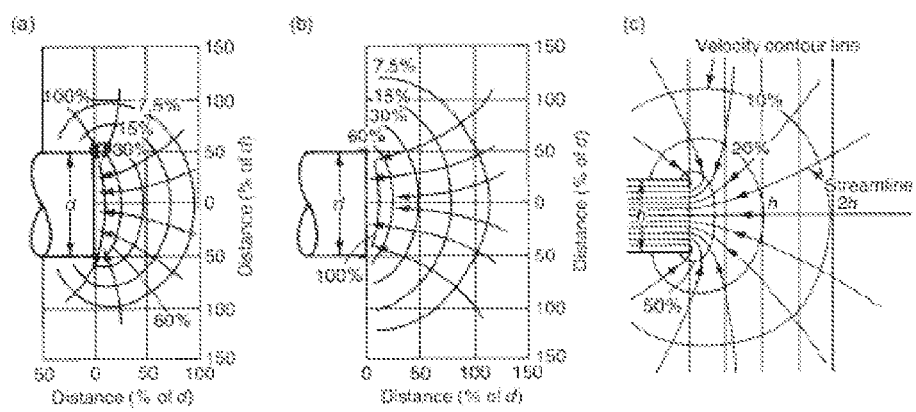
FIG. 24 Air distribution near the position of an exhaust which aspirates air.

FIG. 24 illustrates air distribution near the position of an exhaust which aspirates air. Velocity contours of the air aspirated by the exhausts are indicated for circular and slot inlets. (a) sharp-edged opening; (b) flanged opening; and (c) two-dimensional opening. The arrows indicate the air movement. The circular markings are indicated by the reduced velocity of the air in respect of the velocity at the inlet of the exhaust.

Figure 25:
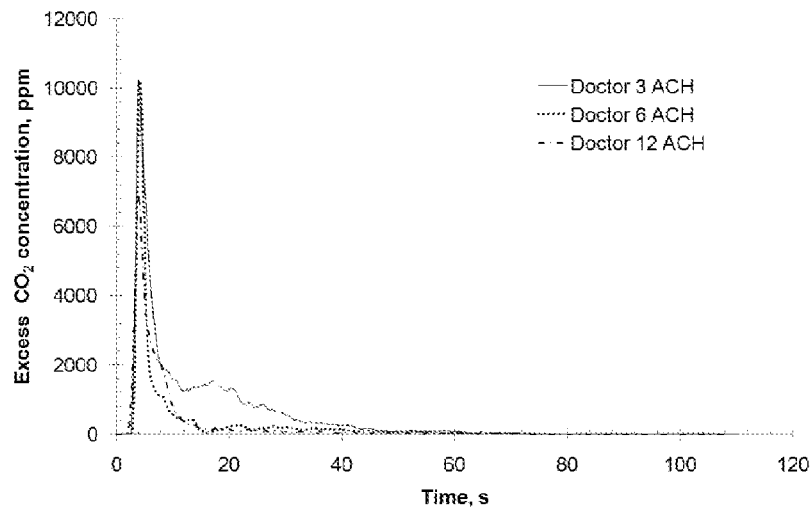
FIG. 25 Exposure of the doctor to coughed pathogen laden air when standing 0.55 m in front of the "coughing patient" in a hospital room ventilated at air changes per hour (ACH) of 3, 6 and 12 $h^{-1}$.

FIG. 25 illustrates $CO_2$ concentration change in time at the mouth of a "doctor" standing 0.55 m in front of a "coughing patient" in a hospital mock-up room ventilated at air changes per hour (ACH) of 3, 6 and 12 $h^{-1}$. No filtration/ventilation unit is present. The set-up is generally described in the examples. Even at 12 ACH 6,400 ppm of $CO_2$ is measured at the mouth of the doctor.

Figure 26:
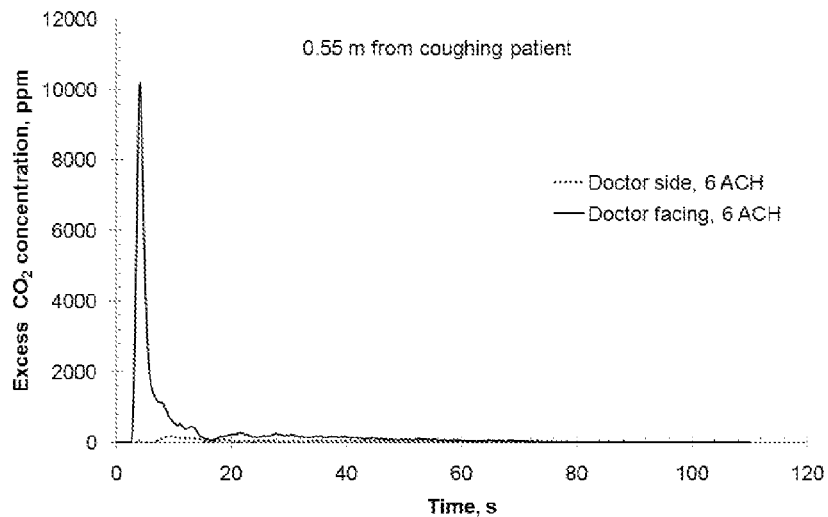
FIG. 26 Exposure of the doctor to coughed pathogen laden air when standing sideways to a coughing patient lying on one side and coughing against the doctor and a second patient.

FIG. 26 illustrates $CO_2$ concentration change in time at the mouth of the "doctor" standing sideways and viewing the two patients. Coughing patient is lying on one side and coughing against the second patient. A much lower $CO_2$ concentration is measured when the doctor is standing sideways when compared to when the doctor is facing/viewing the patient. No filtration/ventilation unit is present. The set-up is generally described in the examples.

Figure 27:
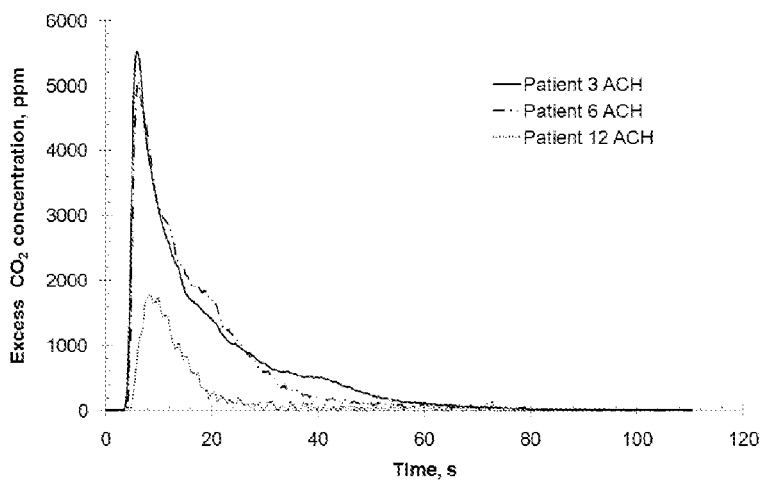
FIG. 27 Exposure of the doctor to coughed pathogen laden air when standing illustrates $CO_2$ concentration change in time at the mouth of the "exposed patient" lying in the second bed and facing the coughing patient lying on one side. Results obtained at three different air changes per hour (ACH)—3, 6 and 12 $h^{-1}$ are compared.

FIG. 27 illustrates $CO_2$ concentration change in time at the mouth of the "exposed patient" lying in a second bed and facing the coughing patient lying on one side and coughing towards the "exposed patient". No filtration/ventilation unit is present. Results are obtained at three different air changes per hour (ACH) of 3, 6 and 12 $h^{-1}$ are compared. At the "exposed patient" a maximum $CO_2$ concentration of 1,800 to 5,600 ppm were measured. The set-up is generally described in the examples.

Figure 28:
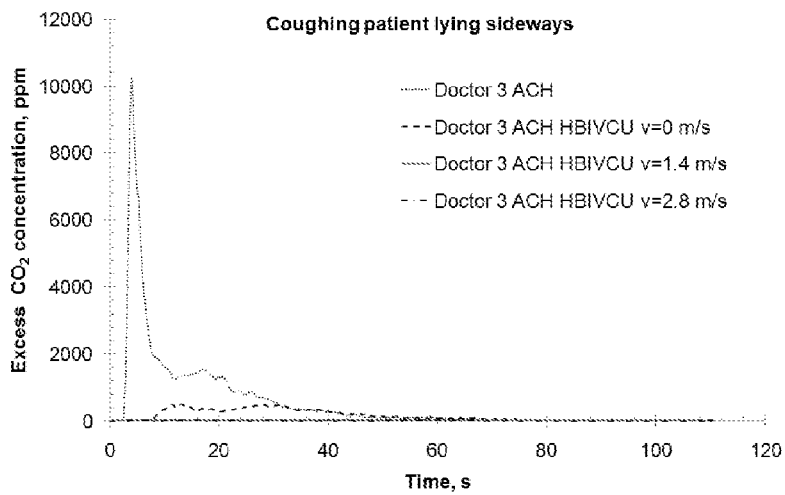
FIG. 28 Exposure of the doctor to coughed pathogen laden air when standing at distance of 0.55 m from a coughing patient, a) when lying facing the doctor and b) when lying on back and coughing upwards, and c) at the mouth of the exposed patient in the second bed.
Figure 28:
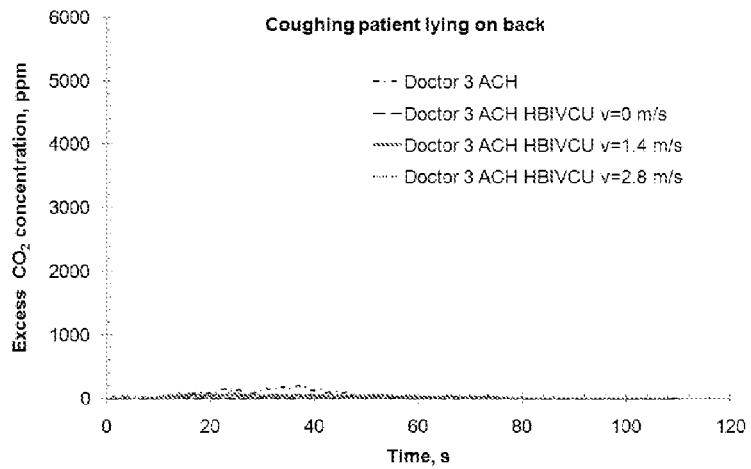
Figure 28:
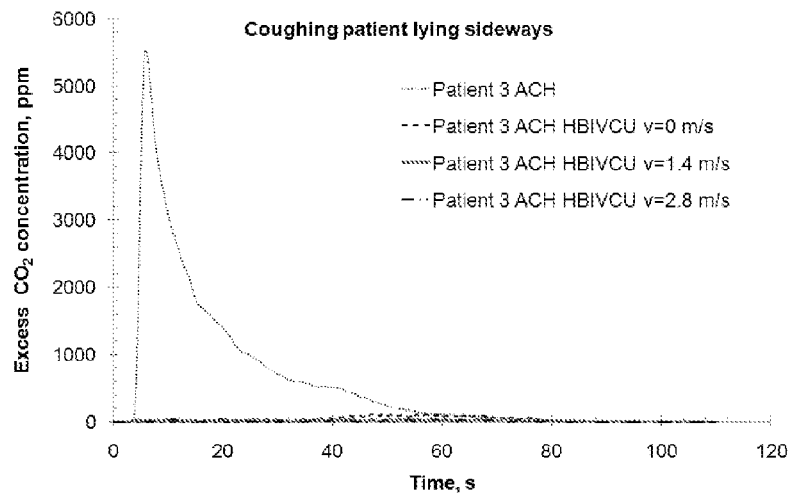

FIG. 28 illustrates CO$_2$ concentration change in time at the mouth of a "doctor" standing at distance of 0.55 m from a coughing patient, a) when the patient is lying facing the doctor and b) when the patient is lying on its back and coughing upwards, and c) at the mouth of the exposed patient in the second bed. The results were obtained at 3 h$^{-1}$ (air changes per hour, ACH) with the filtration/ventilation unit (HBIVCU) at discharge velocity of 0 m/s (HBIVCU is obstacle), 1.8 m/s and 2.8 m/s. Also the reference case without a filtration/ventilation unit (HBIVCU) is illustrated. The set-up is generally described in the examples.

Figure 29:
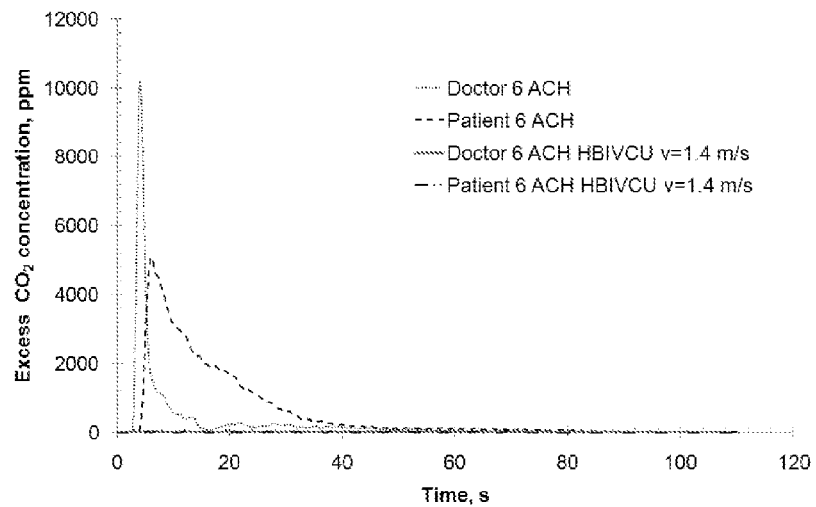
FIG. 29 Exposure of a doctor and a patient to coughed pathogen laden air. The coughing patient lies on its side and is facing the doctor and the second patient.

FIG. 29 illustrates CO$_2$ concentration change in time at the mouth of a "doctor" standing at distance of 0.55 m from a coughing patient and at the mouth of an exposed patient in a second bed. The coughing patient lies on its side and is facing the doctor and the second patient. The results were obtained at ACH of 6 h$^{-1}$ with the filtration/ventilation unit (HBIVCU) at discharge velocity of 1.4 m/s. The reference cases without a filtration/ventilation unit (HBIVCU) and an ACH of 6 h$^{-1}$ are also illustrated. The set-up is generally described in the examples.

Figure 30:
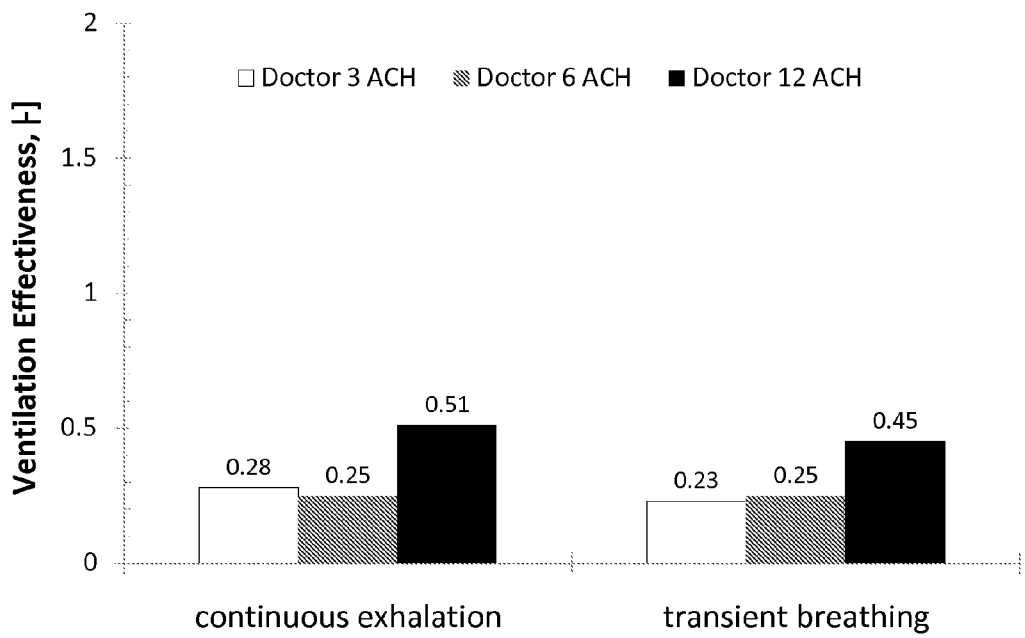
FIG. 30. Ventilation effectiveness at the breathing zone of a "doctor" when standing at distance 0.55 m from a breathing sick patient and facing it.

FIG. 30. Results from example 3. Ventilation effectiveness at the breathing zone of the "doctor" when standing at distance 0.55 m from the breathing sick patient and facing it. The ventilation effectiveness for two breathing modes, continuous exhalation and transient breathing (2.5 s inhalation, 2.5 s exhalation and 1 s break) is shown at different background ventilation rates.

Figure 31:
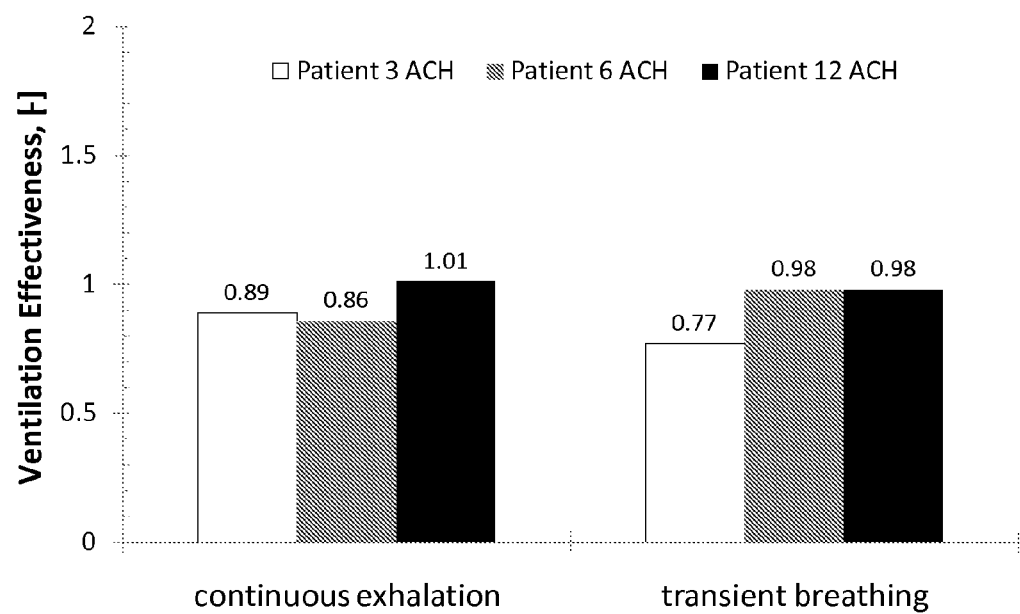
FIG. 31. Ventilation effectiveness at the breathing zone of the second/"exposed" patient, when lying in a bed at distance 1.3 m from the infected patient and facing the infected patient.

FIG. 31. Results from example 3. Ventilation effectiveness at the breathing zone of the second/"exposed" patient, when lying in a bed at distance 1.3 m from the infected patient and facing the infected patient. The ventilation effectiveness for two breathing modes, continuous exhalation and transient breathing (2.5 s inhalation, 2.5 s exhalation and 1 s break) is shown at different background ventilation rates.

Figure 32:
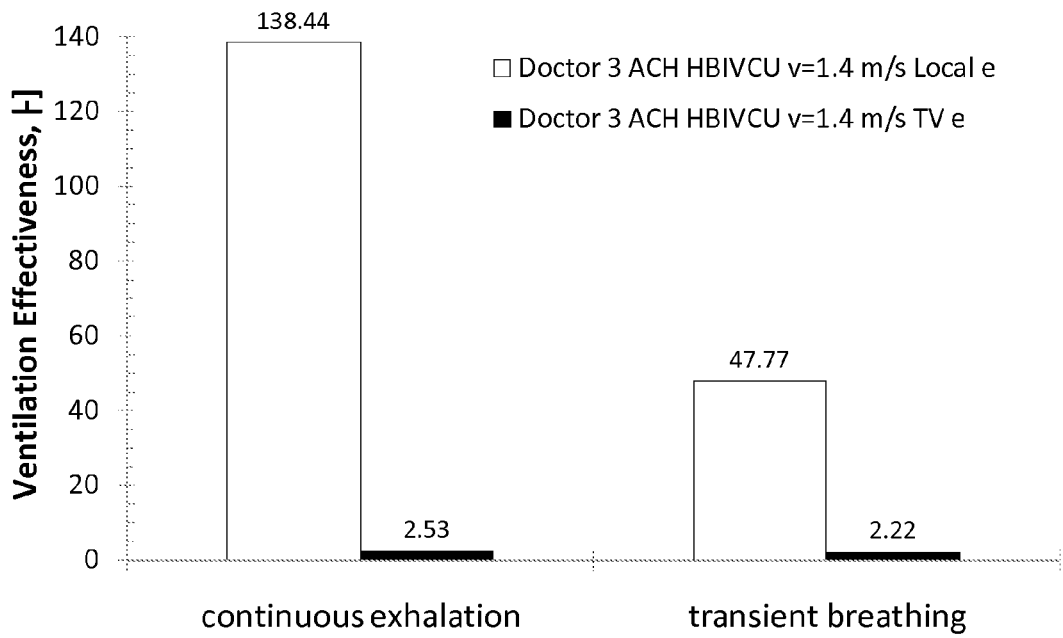
FIG. 32. Ventilation effectiveness at the breathing zone of the "doctor", when standing at distance 0.55 m from the breathing sick patient and facing the sick patient. The results are obtained with the filtration/ventilation unit (HBIVCU) installed on both sides of the bed.

FIG. 32. Results from example 3. Ventilation effectiveness at the breathing zone of the "doctor", when standing at distance 0.55 m from the breathing sick patient and facing the sick patient. The results are obtained with the filtration/ventilation unit (HBIVCU) installed on both sides of the bed. The ventilation effectiveness for two breathing modes, continuous exhalation and transient breathing (2.5 s inhalation, 2.5 s exhalation and 1 s break) is shown at different background ventilation rates.

Figure 33:
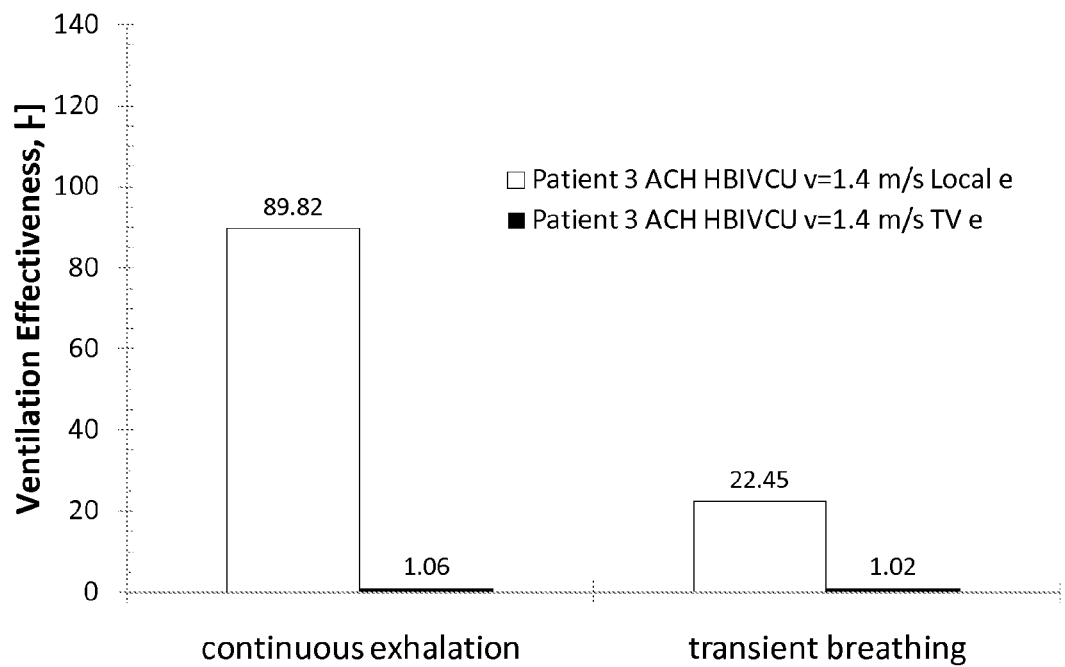
FIG. 33. Ventilation effectiveness at the breathing zone of the second, "exposed" patient, when lying in a bed at distance 1.3 m from the infected patient and facing the patient. The results are obtained with the filtration/ventilation unit (HBIVCU) installed on both sides of the bed.

FIG. 33. Results from example 3. Ventilation effectiveness at the breathing zone of the second, "exposed" patient, when lying in a bed at distance 1.3 m from the infected patient and facing the patient. The results are obtained with the filtration/ventilation unit (HBIVCU) installed on both sides of the bed. The ventilation effectiveness for two breathing modes, continuous exhalation and transient breathing (2.5 s inhalation, 2.5 s exhalation and 1 s break) is shown at different background ventilation rates.

EXAMPLES

Coughing is the most obvious symptom of a respiratory disease, therefore the experiments has been performed with the simulation of coughing persons i.e. by "coughing dummies". Coughing is an impulse jet led by a characteristic vortex ring that can penetrate quite far before it dissolves in the surrounding air. The peak velocity when coughing can vary from 6 m/s to 30 m/s. A cough can include up to 2085 droplets with a concentration of 5.2 per cm$^3$ per cough. Due to its high initial momentum the cough becomes one of the dominating transport mechanisms indoors for airborne particles generated from a coughing diseased individual.

Breathing is the natural process of existence: every minute 6 liters of air pass through the human lungs as a result from breathing, at normal sedentary activity, making this natural pulmonary process quite important for the air flow distribution around the human body. Both exhalation from mouth and nose have quite high initial momentum and are able to penetrate the free convective layer surrounding the human body. All pollutants and particulate matter generated from exhalation therefore are pushed away from the body and very little amount is re-inhaled or pulled back by the convective layer. One of the most common ways of droplet and sub-micron particles generation is through exhalation. When person is sick this particulate matter is laden with pathogens.

Example 1

This example describe the results obtained with a setup as illustrated in FIGS. 4a and 4b and the results shown in FIGS. 5 and 6.

In this example of the invention, a bed integrated filtration/ventilation unit was incorporated within the side head boards of a hospital bed and the filtration/ventilation unit exhausted the air from the pulmonary activities of the patient (breathing, coughing, sneezing etc, cleansed the air from the presence of pathogens and other health-hazardous matter (toxins), then discharged the air vertically through a horizontal slot, and at a high initial velocity towards the ceiling where it was exhausted by the total volume ventilation. The system can be designed to run in conjunction with total volume ventilation as shown in FIG. 4.

The filtration/ventilation unit of the experiment consisted of two linear units with fans (low energy consumption and low noise level) installed in the side elements of each unit. Exhaled/coughed air from a patient was sucked through the two sided suction openings placed on left and right side cabinets (next to the head of the patient in the bed). The air was cleaned and discharged upward from the horizontal slots placed on top of the same boards.

Cleaning units consisting of UV-C light emitting diodes/lights, and HEPA filters were placed in the side cabinets (units), so as to catch the pathogens and health-hazardous matter on release and purge them. This would implement the usage of small filters, which would also be easy to change, hereby reducing the risk of release of pathogens (the filter is in the infectious isolation unit itself).

After being cleansed the air was exhausted/directed upwards at high velocities (e.g. about 3 m/s). To increase the efficiency of the filtration/ventilation unit the suction area (inlet slot) was bigger than the room discharge orifices (outlet slot): to cover bigger area and also to have a low suction velocity so that the UV-C light was more effective on single pass (≈0.5 m/s). To improve further the efficiency of the UV-B/C light the inside of the side cabinets could be lined with highly reflective surface.

Performance Efficiency of the Filtration/Ventilation Unit

In this example the filtration/ventilation unit has been studied by computer simulations: Computational Fluid Dynamics (CFD). One patient was assumed to do "continuous coughing" at a speed of 22 m/s. The CFD simulation adopted the standard Reynolds number k-ε model (Launder and Spalding, 1974) and implicit SIMPLE algorithm (Patankar, 1980). Moreover, the finite volume method with a first-order upwind scheme (UD) was adopted for discretizing the governing equations. The results of the simulations performed with commercially available software for CFD, namely STARCD, showed that the proposed filtration/ventilation unit was advantageous over the conventional ventilation practice of mixing ventilation in infectious isolation units. The simulation results revealed that the filtration/ventilation unit in conjunction with mixing ventilation used at only 6 air changes per hour (FIG. 1b) will be able to reduce the background concentration of pathogens generated by the patient in the bed due to respiration activities (breathing, coughing) substantially in comparison with mixing ventilation alone (FIG. 4a) working at 12 air changes per hour (minimum requirement in present standards and guidelines for isolation rooms in hospitals).

FIGS. 5 and 6 show some of the simulation results obtained for a room with two patients. The spread of the air coughed from one lying patient to the room and to another patient is shown in the figures. Different iso-contours and grayscale are used to define the concentration of coughed air in the room (in percent when the numbers are multiplied by 100). The spread of coughed air in two planes in the room are shown: vertical plane—at the location of the head of the coughing patient (FIGS. 5a and 6a referred as 0.2x) and horizontal plane—at the location of the mouth of the coughing patient (FIGS. 5b and 6b referred as 0.66 z). The comparison of the results shows drastic reduction in the spread of coughed air in the room with the proposed filtration/ventilation unit, i.e. drastic reduction of the risk of airborne transmission of diseases. The simulation indicates that 8% of the pathogens and other health-hazardous matter being present in the coughed air of a patient could pass to the area around the head of another patient if no filtration/ventilation unit was used. When a filtration/ventilation unit was used less than 2%, i.e. four times less, of the pathogens and other health-hazardous matter being present in the coughed air would pass to the other patient.

Example 2

A set of experiments were performed to prove the effectiveness of the bed incorporated device. The measurements were commenced in a climate chamber that simulated a hospital isolation room with two beds with patients (FIG. 9). Mixing ventilation with one rectangular supply diffuser and 2 rectangular exhaust units installed on the ceiling was used to ventilate the room. The supply air diffuser was positioned in the center of the ceiling, while the 2 exhausts were positioned with one above each bed and above the head of each dummy (patient).

FIG. 9 shows the set-up during the experiments. Coughing dummy (1) facing the doctor (thermal manikin) (2) and "exposed" dummy (3) on second bed.

Two scenarios were examined: scenario 1—two patients and a doctor were simulated and scenario 2—only two patients. During the experiments with scenario 1 the doctor was simulated by a thermal manikin with body size and shape as an average Scandinavian woman. The two patients were simulated by 2 thermal dummies with a shape closely resembling the one of the human body. Both dummies were lying in the beds: one in each bed. One of the dummies was equipped with a coughing machine used to generate a cough. The generated cough ("mouth" opening with diameter of 21 mm and cough volume of 2.5 L/cough) consisted of 100% $CO_2$ gas that was used to simulate the aerosol release as a result from the cough (it is assumed that aerosols smaller than 2 μm are airborne and behave as the tracer gas). The heat generated by the manikin and the dummies was similar to the heat generated by a person at low activity level. During the experiments with scenario 2 the thermal manikin was used to simulate the exposed patient.

Four filtration/ventilation units, 2 at each bed and positioned on each side of the bed at the location of the head of the "patient" lying in each bed were used to test the efficiency of the units with respect to evacuating the coughed air. For the experiment the 4 bed integrated hospital units (filtration/ventilation units) were connected to a separate supply and exhaust system, but in reality those could re-circulate and cleanse the room air via a set of HEPA/ULPA filters and UVGI units installed in them. This would allow for re-circulation of the room air and further utilization and realized energy savings. The units could also be connected to the total volume exhaust system as well.

To validate whether or not the bed incorporated cleansing unit helped in reducing the risk from infections for the medical staff taking care for the sick people in an isolation room, the level of $CO_2$ was measured at the mouth of the thermal manikin representing the doctor (scenario 1—FIG. 10). For this purpose the thermal manikin was positioned close to the bed with the "coughing" dummy. In this case the dummy was facing the doctor. The horizontal distance from the simulated mouth opening of the coughing machine and the body plane of the manikin was kept constant at 0.55 m. During the measurements with scenario 2 the thermal manikin simulated a patient lying in the bed next to the "coughing patient", i.e. the dummy with the coughing machine (FIG. 12). In this case the coughing dummy and the thermal manikin were facing each other. The mouth of the thermal manikin ("exposed patient") was aligned with the release opening of the coughing machine, i.e. on the axis of the released jet. The distance between the two beds was kept at 1.3 m. The "doctor" was not present in the room. The aim was to study the effectiveness of the filtration/ventilation units to stop the penetration of the coughed jet into the isolation room/occupied space and to protect the second patient from being re-contaminated, especially if the stage of the infectious disease is different for the two patients in the room: one almost cured and one at incubation stage. This latter case would more closely represent the situation in a case of epidemic or even pandemic where many people would be kept in close proximity with each other and at different stages of the disease advancement.

FIG. 10 illustrates the set-up during scenario 1: two patients (coughing patient (1) and second patient (3)) and a doctor (2) near the coughing patient (1). The doctor is exposed to coughed air. 4 is TV supply diffuser and 5 is TV exhaust diffuser.

FIG. 11 illustrates scenario 1: Two patients (coughing patient (1) and second patient (3)) and a doctor (2) near the coughing patient (1). The doctor is protected from the coughed air by the cleansing devices (6). 4 is TV supply diffuser and 5 is TV exhaust diffuser.

FIG. 12 illustrates the set-up during scenario 2: a) Only two patients in the room. The coughing patient (1) and the "exposed" patient (2) are facing each other. 4 is TV supply diffuser and 5 is TV exhaust diffuser.

FIG. 13 illustrates scenario 2 set up with only two patients in the room. The coughing patient (1) and the "exposed" patient (2) protected by the cleansing devices. The "exposed" patient (2) is protected from the coughed air by the cleansing devices (6). 4 is TV supply diffuser and 5 is TV exhaust diffuser.

The results obtained with the cleaning devices (filtration/ventilation units) were compared with a reference case without cleaning units when the chamber was ventilated at 3 or 6 or 12 ACH, where 12 ACH is the minimum ACH rate recommended in the present standards (ASHRAE 170-2008) for ventilation of infectious wards. The room temperature was kept at 22° C. The 12 ACH corresponded to 184 L/s±3 L/s and the exhausted amount of air was set to 195 L/s which gave an under-pressure in the chamber of 1.6 Pa relative to the surroundings. The measurements with cleaning units were performed when the chamber was ventilated at 3 ACH (46 L/s±3 L/s) for the air supplied and exhausted air was 55 L/s so as to give the same under-pressure of 1.6 Pa.

FIG. 14 presents the results obtained from the measurements with scenario 1, i.e. the case when the two dummies were in beds and the thermal manikin was representing a doctor standing next to the bed of the coughing "patient". It can be clearly seen that in the reference case "the doctor" is highly exposed to the coughed pathogen laden air (the stippled line indicated by 12 ACH): the concentration of $CO_2$ measured at the mouth of the manikin is 8 times higher than the background concentration of $CO_2$. However when the cleaning units are installed by the head-side of the bed of "the coughing patient" and are operated at 1.4 m/s exit velocity, the concentration of $CO_2$ measured at the mouth was the same as in the background, i.e. no coughed air reached the doctor (the solid line indicated by 3 ACH and Hospital Box), i.e. the coughed air was exhausted by the bed integrated cleansing unit (FIG. 14).

Improvement with the cleaning devices was observed also in scenario 2 when a patient was lying in a bed next to the coughing patient, i.e. when the thermal manikin was placed in the neighboring bed (FIG. 15). At the reference case (scenario 2) however the concentration of $CO_2$ in the air inhaled by the laying thermal manikin was measured 2 times lower than in the case with the standing "doctor" (scenario 1) (the stippled line indicated by 12 ACH). This was because the distance between the two beds was relatively long, so the coughed air jet was partly diluted by the time it reached the breathing zone of the lying thermal manikin. Still the $CO_2$ concentration in the air inhaled by the patient was quite high. It may be expected that for certain diseases which are with high infectivity risk/virulence (tuberculosis, SARS corona viruses etc) this could cause contamination or re-contamination. Also in case of epidemic/pandemic when people are placed in the same room, airborne cross-infection even of healthy people who will be miss-diagnosed due to similar symptoms of some benign forms of a disease (in Hong Kong during the SARS outbreak people not infected with SARS but with symptoms similar to these of SARS were hospitalized and placed in the same room as SARS patients). As can be seen from the results in the figure (the solid line indicated by 3 ACH and Hospital Box), the use of the cleaning devices was efficient and almost no coughed air was inhaled by the "exposed patient", the concentration of $CO_2$ measured at the mouth of the thermal manikin were as the background level of the gas.

The results of the measurements demonstrate the great potential of the cleaning device in effective capturing and evacuating the airborne pathogens released due to respiration activities of sick people in isolation hospital wards. This will lead to reduction of the risk from airborne transmission of contagious diseases for the medical personal as well as the other patients. The performance of this device would lead to certain energy savings realized due to the lower amounts of clean air supplied by the total volume ventilation (only 3 ACH) compared to the recommended today 12 ACH. Additional saving due to reduced initial investment costs (use of multi-bed isolation rooms instead of single bed rooms, reduced space for ducting, smaller HVAC units, etc.) can be achieved as well.

Further experiments showing the effect of the ventilation unit as described herein will be presented by Zhecho Bolashikov in a Ph.D.-thesis at the Technical University of Denmark. This thesis further describes the conditions when performing the test. The conclusions in this thesis are given below.

The risk of airborne cross-infection due to pathogens generated during coughing was studied in a full scale mock-up of a hospital room with two patients lying in beds and a standing doctor. The following conclusions can be drawn from the experiments performed without using the ventilation unit as described herein:

Regardless of the flow rate supplied by the background ventilation in a hospital room there is enhanced risk from airborne cross infection for the medical staff standing in close proximity to a coughing patient;

Elevated background ventilation rates may increase the risk of cross-infection in an occupied place, up to a certain distance downstream of the coughed air. This is because the high velocities of the coughed air can peel off the boundary layer produced by the background ventilation system and leave the person exposed to the coughed flow with high concentration of pathogens. After this distance the higher flow rates of the background ventilation result in better dilution of the air from the coughed flow and a lower risk from cross infection.

When the distance between the sick person and the doctor/nurse increases the risk of the doctor being exposed to contaminated coughed air decreases when comparing experiments performed with similar background ventilation flow rate. The reduction of risk is due to dilution of the air;

The posture of the coughing patient and the location of the doctor are important factors: maximal exposure occurs when the doctor is facing the coughed patient. Standing sideways of the coughing person decreases substantially the exposure risk. The risk of direct exposure to coughed air is minimal when the coughing person lies on his/her back;

The recommendations in the present standards and guidelines air change rate of 12 h-1 does not reduce the risk of airborne cross-infection. Thus the present air distribution or ventilation methods in hospitals are not efficient for reducing the spread of air-borne diseases.

When performing similar experiments using the ventilation unit as described herein for reducing the risk of airborne cross infection by local ventilation at the vicinity of the bed of a coughing sick patient in a hospital room, the following conclusions could be made:

The use of the ventilation unit acts as protective means against exposure of closely standing occupants to coughed air from the patient lying in the bed;

The performance of the ventilation unit is unaffected by the rate of the background ventilation flow if the local suction of the ventilation unit is strong enough or the ventilation unit is located close enough to the pollution source i.e. close enough to the head of the patient;

With respect to coughed air the background ventilation rate of 12 $h^{-1}$ as used today for ventilation of infectious hospital wards can be substantially lowered and the risk of airborne cross-infection reduced when the ventilation unit is used to produce an air curtain. This strategy may also lead to energy savings.

Example 3

A set of experiments were performed to demonstrate the ability of the bed incorporated filtration/ventilation unit to evacuate the exhaled infected air in case of breathing. The set up of the experiment resembled very much the one described in Example 2 (FIG. 9). In this case 2 thermal manikins were used: one to resemble the doctor and a second one to mimic the sick patient spreading the diseases.

FIG. 9 shows the set-up during the experiments. Coughing dummy (1) changed with breathing thermal manikin facing the doctor (second thermal manikin) (2) and "exposed" dummy (3) on second bed.

Two scenarios were examined: 1—two patients and a doctor, and 2—only the two patients in the room. During the experiments in scenario 1 (FIG. 10) the doctor (2) was simulated by a thermal manikin with realistic body shape. The infected patient was substituted with a second breathing thermal manikin (1). The second patient was a thermal dummy (3) with a simplified body shape but close to that of the human body. The "patients" were both lying in beds. The thermal manikin simulating infected patient was equipped with an artificial lung that heated and supplied the exhaled air though the mouth at the same conditions as the real air exhaled by a human (Melikov 2004, Melikov and Kaczmarczyk 2007). The lung was used to simulate the breathing cycle of an average person at rest: 6 l/s with 2.5 s inhalation, 2.5 s exhalation and 1 s break (Hyldgaard 1998). The air exhaled was marked with R134a tracer gas (Freon) to mimic the aerosol release as a result from breathing. The experiments performed under different conditions (as specified in the following) were also repeated with continuous exhalation in order to study the case of maximum exposure to the pathogens, peak of tidal exhalation at the mouth of the health care worker or other patient. The positioning of the filtration/ventilation unit as well as their operation was the same as described in Example 2. To validate whether or not the filtration/ventilation unit helped to reduce the risk from infection for the doctor (can be other health care worker) the tracer gas concentration was measured at the mouth of the thermal manikin 2 (scenario 1—FIG. 10). The doctor was placed facing the infected patient (manikin 1) and at a distance 0.55 m from mouth opening.

During the measurements with scenario 2 (FIG. 11) the thermal manikin used in scenario 1 to simulate the doctor was used to mimic the second/exposed patient lying in the second bed. The distance between the two beds was kept constant and 1.3 m. The two manikins were placed lying facing with their mouths aligned. The "doctor" was not present in the room. The aim of these sets of experiments was to show the effectiveness of the filtration/ventilation unit in stopping the spread and dispersion of the exhaled pathogen laden air into the hospital room and thus to protect other occupants/patients from being re-infected, provided that the two patients are at different stages of the disease: one close to recovering and one still infectious. This is relevant in cases of epidemics or even pandemics, where many people will be placed together and in close proximity at different stages of the disease advancement and some may even be miss-diagnosed due to similar symptoms.

FIG. 10 illustrates the set-up during scenario 1: breathing thermal manikin (1), i.e. the infected patient (1), the second patient (3) and a thermal manikin (2), i.e. a "doctor" near the breathing manikin (1). The doctor is exposed to exhaled air. The background ventilation air supply diffuser (4) and air exhaust diffuser (5) are indicated in the figure as well.

FIG. 11 illustrates scenario 1: breathing thermal manikin (1), i.e. infected patient, the second patient (3) and the doctor (2) near the breathing patient (1). In this case the cleansing devices (6) are installed on the bed of the infected patient. The background ventilation air supply diffuser (4) and air exhaust diffuser (5) are indicated in the figure as well.

FIG. 12 illustrates the set-up during scenario 2, when only two persons are present in the room: breathing thermal manikin (1), i.e. infected patient and a thermal manikin (2), i.e. "exposed" patient lying on the second bed. The two manikins are facing each other. The background ventilation air supply diffuser (4) and air exhaust diffuser (5) are indicated in the figure as well.

FIG. 13 illustrates scenario 2 set up with only two patients in the room. The breathing patient (1) and the "exposed" patient (2) protected by the cleansing devices. The "exposed" patient (2) is protected from the exhaled air by the cleansing devices (6). 4 is TV supply diffuser and 5 is TV exhaust diffuser.

In order to evaluate the performance of the filtration/ventilation unit the ventilation effectiveness was calculated (CEN CR 1752-1998). It measures the relationship between the pollutant concentration in the exhaust air and the pollutant concentration at the measured point.

$$\varepsilon_v = \frac{C_e - C_s}{C_i - C_s}$$

$\varepsilon_v$—is the ventilation effectiveness;
$C_e$—is the pollution concentration in the exhaust air;
$C_s$—is the pollution concentration in the supply air;
$C_i$—is the pollution concentration at the "i"th measured point.

The ventilation effectiveness depends on the air distribution in the room and the location of the pollution source in the space. If there is complete mixing of the air and the pollutants, the ventilation effectiveness is 1. If the air quality at the measured point "i" is higher than in the exhaust (lower pollution level measured at point "i") the effectiveness is higher than 1. Ventilation effectiveness lower than 1 means that the pollutant is not effectively evacuated from the space. Usually the ventilation effectiveness ranges from 0.4 (mixing ventilation) to 1.4 (displacement ventilation), CEN CR 1752-1998.

The ventilation effectiveness at the mouth of the "doctor" (scenario 1 and at the mouth of the "second, exposed patient" obtained with the ventilation/cleaning unit was compared with the reference case when bed without filtration/ventilation units were used. The comparison was performed at three different ventilation rates, corresponding to 3, 6 and 12 air changes per hour (ACH). All other conditions were kept the same as already specified in Example 2.

FIG. 30 presents the ventilation effectiveness obtained from the measurements with scenario 1 and scenario 2. At 3 and 6 ACH the ventilation effectiveness at the mouth of the "doctor" (scenario 1) is quite low (around 0.3) due to the fact that the existing convective layer around "doctor's" body captures most of the exhaled pathogens and transports them into the breathing zone of the doctor making it quite risky for acquiring an airborne infection. At 12 ACH the effectiveness is doubled due to the elevated background velocities and the improved dilution in the room. The ventilation effectiveness obtained in scenario 2 at the mouth of the second "the exposed" patient is higher but still lower than 1 (FIG. 31). This is due to the fact that the distance between the two patients is relative long. The increase of the air change rate to 12 leads only to a small increase of the ventilation effectiveness.

The use of the filtration/ventilation unit (named here as HBIVCU, i.e. Hospital Bed Integrated Ventilation Cleansing Unit) helps to evacuate of the exhaled air by the sick patient (FIGS. 32 and 33). The substantially higher ventilation effectiveness at the mouth of the "doctor" (FIG. 32) and at the mouth of the "exposed patient" (FIG. 33) shows that only very small amount of the exhaled "infected" air escapes to be locally captured by the HBIVCU.

The following conclusions can be drawn from the experiments performed without using the ventilation unit as described herein:

Regardless of the flow rate supplied by the background ventilation in a hospital room, there is enhanced risk from airborne cross infection for the medical staff standing in close proximity to a breathing patient;

The recommendations in the present standards and guidelines air change rate of 12 h-1 does not reduce the risk of airborne cross-infection even in the case of breathing, i.e. exhaled flow with low initial momentum. Thus the present air distribution or ventilation methods in hospitals are not efficient for reducing the spread of air-borne diseases.

The use of the filtration/ventilation unit HBIVCU reduces substantially the risk of cross-infection for medical staff standing close to infected patients as well as for other patients in the room.

The use of the HBIVCU may lead to substantial lowering of the background ventilation rate of 12 ACH as required today for ventilation of infectious hospital wards at lower risk of airborne cross-infection. This strategy may also to energy saving, low initial investment and easy and inexpensive maintenance.

The invention claimed is:

1. A method for partly isolating an area of a bed having a head region, said method comprising:
   localising an area which is to be partly isolated,
   providing at least one filtration/ventilation unit around or in connection to said area, wherein said filtration/ventilation unit is an integrated part of said bed or releasably mounted on said bed,
   aspirating air from said area into said at least one filtration/ventilation unit, and cleaning said air inside the filtration/ventilation unit,
   directing cleansed air out of said at least one filtration/ventilation unit in a horizontal to upward direction, thereby forming an air curtain of upwardly flowing air, extending within 20° into or away from the area with respect to vertical extensions of the sides of the bed, thereby
   partly isolating the area and removing microorganisms or viruses in air from the area.

2. A bed with at least one filtration/ventilation unit located at least at a region of a bed, where said at least one filtration/ventilation unit is an integrated part of said bed or said at least one filtration/ventilation unit is releasably mounted on said bed such that said at least one filtration/ventilation unit can be repositioned together with said bed and be raised and lowered together with said region, said at least one filtration/ventilation unit being adapted to isolate a subject lying in the bed from the surroundings by generating at least one air curtain of upwardly flowing cleansed air, and being adapted to aspirate and clean contaminated air from said region.

3. The bed according to claim 2, having a head region and comprising at least two filtration/ventilation units, said ventilations units being located at least one filtration/ventilation unit at each side of said head region of said bed and/or further comprising a filtration/ventilation unit at at least one end of the bed.

4. The bed according to claim 2, wherein said at least one filtration/ventilation unit is connected to said bed so as to allow adjustment of the unit in the direction up/down and/or forward/backward relative to the bed.

5. The bed according to claim 2, wherein said bed is a bed for prolonged rest of a human.

6. The bed according to claim 2, wherein said at least one filtration/ventilation unit produces an air curtain across the bed between an air slot directing air out of a filtration/ventilation unit and an air slot directing air into a filtration/ventilation unit thereby isolating at least part of the bed from the surroundings.

7. The bed according to claim 2, wherein said filtration/ventilation unit further comprises
   means for controlling the direction of the outlet air and/or
   means for controlling the velocity of the outlet air.

8. A method for protecting personnel working with at least one patient by establishing at least one air curtain produced by a filtration/ventilation unit of claim 1 between the patient and the personnel.

9. The bed of claim 2, wherein the air curtain is vertical upward or diagonal upward.

10. The bed of claim 2, wherein the air curtain is horizontal.

11. The bed of claim 2, wherein the at least one filtration/ventilation unit comprises a source of electromagnetic radiation capable of disinfecting contaminated air.

12. The bed of claim 2, wherein the at least one filtration/ventilation unit comprises a filter for cleaning contaminated air.

13. The bed of claim 2, wherein the ventilation/filtration unit comprises sensors to determine the position of a subject's head and is capable of regulating the direction or velocity of air in response to the sensors' determination.

14. The bed of claim 2, wherein the ventilation/filtration unit provides the isolated region with gas of a controlled composition.

15. The bed of claim 2, wherein the ventilation/filtration unit is capable of drying and humidifying air supplied to the isolated region.

16. The method according to claim 1, wherein the area to be partly isolated is the head region of the bed.

* * * * *